US012766113B2

(12) United States Patent
Golczak et al.

(10) Patent No.: US 12,766,113 B2
(45) Date of Patent: Oct. 20, 2026

(54) CELLULAR RETINOID BINDING PROTEIN ANTAGONISTS AND USES THEREOF

(71) Applicant: CASE WESTERN RESRVE UNIVERSITY, Cleveland, OH (US)

(72) Inventors: Marcin Bernard Golczak, Cleveland, OH (US); Josie Ann Silvaroli, Cleveland, OH (US)

(73) Assignee: CASE WESTERN RESERVE UNIVERSITY, Cleveland, OH (US)

(*) Notice: Subject to any disclaimer, the term of this patent is extended or adjusted under 35 U.S.C. 154(b) by 1248 days.

(21) Appl. No.: 15/734,781

(22) PCT Filed: Jun. 7, 2019

(86) PCT No.: PCT/US2019/035986

§ 371 (c)(1),
(2) Date: Dec. 3, 2020

(87) PCT Pub. No.: WO2019/236962

PCT Pub. Date: Dec. 12, 2019

(65) Prior Publication Data

US 2021/0228500 A1 Jul. 29, 2021

Related U.S. Application Data

(60) Provisional application No. 62/681,984, filed on Jun. 7, 2018.

(51) Int. Cl.
*A61K 31/05* (2006.01)
*A61P 27/02* (2006.01)

(52) U.S. Cl.
CPC .............. *A61K 31/05* (2013.01); *A61P 27/02* (2018.01)

(58) Field of Classification Search
CPC ................................ A61K 31/05; A61P 27/02
See application file for complete search history.

(56) References Cited

U.S. PATENT DOCUMENTS

| | | | | |
|---|---|---|---|---|
| 7,432,307 | B2 | 10/2008 | Mata et al. | |
| 9,254,272 | B2 | 2/2016 | Mcallister et al. | |
| 10,568,851 | B2 | 2/2020 | Palczewski et al. | |
| 2005/0282912 | A1* | 12/2005 | Chen | A61K 31/05 514/734 |
| 2006/0247321 | A1 | 11/2006 | Chen | |
| 2012/0172339 | A1 | 7/2012 | Makriyannis et al. | |
| 2012/0288568 | A1 | 11/2012 | Widder et al. | |
| 2012/0309835 | A1 | 12/2012 | Widder et al. | |

OTHER PUBLICATIONS

Imamura (Year: 2013).*
Thomas (Year: 2007).*
Rajan (Year: 2016).*
Mo et al (Year: 2004).*
Deiana et al (Year: 2012).*
Zhang (Year: 2004).*
Szczesniak (Year: 2011).*
Kubota et al (Year: 2010).*
Silvaroli et al (Year: 2019).*
Sczcesniak et al. "Nonpsychotropic Cannabinoids, Abnormal Cannabidiol and Canabigerol-Dimethyl Heptyl, Act at Novel Cannabinoid Receptors to Reduce Intraocular Pressure", Journal of Ocular Pharmacology and Therapeutics, 2011, vol. 27(5), pp. 427-435. Entire Document.
Madiera et al. "Contribution of Microglia-Mediated Neuroinflammation to Retinal Degenerative Diseases", Mediators in Inflammation, 2015, Article ID 673090, pp. 1-15. Entire Document.

* cited by examiner

*Primary Examiner* — Jeffrey S Lundgren
*Assistant Examiner* — Ibrahim D Bori
(74) *Attorney, Agent, or Firm* — Tarolli, Sundheim, Covell & Tummino LLP

(57) ABSTRACT

A method of treating an ocular, inflammatory, immune, and/or metabolic disorder in a subject in need thereof includes administering to the subject a therapeutically effective amount of a compound having a structure of formula (I).

4 Claims, 15 Drawing Sheets abn-CBDO CBDO O-1918 limonene

CELLULAR RETINOID BINDING PROTEIN ANTAGONISTS AND USES THEREOF

RELATED APPLICATION

This application claims priority from U.S. Provisional Application No. 62/681,984, filed Jun. 7, 2018, the subject matter of which is incorporated herein by reference in its entirety.

GOVERNMENT FUNDING

This invention was made with government support under Grant Nos. EY023948, awarded by The National Institutes of Health. The United States government has certain rights to the invention.

TECHNICAL FIELD

This application relates to inhibitors (antagonists) of cellular retinoid bind proteins (CRBPs) represented by CRB1, CRBP3, and CRBP4 and their use in treating (i) ocular and/or retinal disorders associated with aberrant all-trans-retinaldehyde (atRAL) clearance and/or formation of retinaldehyde metabolites in the retina, (ii) inflammatory and/or immune disorders associated with or affected by retinoic acid production, as well as (iii) metabolic disorders related to the physiological function of CRBP3 and/or CRBP4 in a subject in need thereof. Additionally, this application relates to compounds and methods of modulating production of bioactive metabolites of vitamin A, including retinoic acid, by administrating CRBP antagonists to a subject.

BACKGROUND

The retinoid (visual) cycle is a complex enzymatic pathway essential for regeneration of the visual chromophore, 11-cis-retinaldehyde, a component of rhodopsin and cone opsins that undergoes activation by light in vertebrate eyes (FIG. 1). In a healthy eye, the proper homeostasis of vitamin A (all-trans-retinol, atROL) supports visual function under a variety of lighting conditions. However, certain environmental insults, including prolonged exposure to intense light in combination with an unfavorable genetic background can overcome the adaptive capabilities of the visual cycle, and thus compromise retinal function. A clinical example is Stargardt disease, an inherited form of juvenile macular degeneration caused by mutations in the photoreceptor-specific ATP-binding cassette transporter (ABCA4). It causes a delay in atRAL clearance and the subsequent formation and accumulation of cytotoxic retinal metabolites. Importantly, even in the presence of a functional retinoid cycle, toxic atRAL condensation product accumulates as reported in patients affected by mutations in the ELOVL4, VMD2 or MERTK genes as well as other forms of hereditary cone-rod dystrophy. Additionally, in patients affected by age-related macular degeneration (AMD), the atrophic lesions are formed in areas of increased accumulation of the aberrant retinaldehyde metabolites. These examples indicate the significance of vitamin A homeostasis for photoreceptor health and suggest that an imbalance in retinoid metabolism is an etiologic factor in retinal degeneration.

Outside of the eye, the vitamin A metabolite all-trans-retinoic acid is an important determinant of intestinal immunity. Retinoic acid, a bioactive metabolite of vitamin A is produced by immune dendritic cells from the gut-associated lymphoid organs activates T cells and appears to be involved in the imprinting of T cells with the gut-homing specificity.

Several mechanisms associated with retinoid metabolism can contribute to retinopathies. For example, mutations in LRAT, STRA6, or RPE65 genes that result in the inability to uptake vitamin A or produce the visual chromophore lead to the early-onset progressive degeneration of photoreceptors. However, even an unaffected retinoid cycle can be a source for cytotoxic metabolites. Despite being essential for vision, retinaldehydes can inflict retinal damage, an outcome observed in Stargardt macular dystrophy and AMD. This toxicity stems from the reactivity of the aldehyde group toward certain cellular nucleophiles, including the amino groups of phospholipids and proteins. Although the formation of the Schiff base adduct of atRAL with phosphatidylethanolamine is reversible, its reaction with a second molecule of retinaldehyde initiates a cascade of irreversible nonenzymatic conversions that lead to the formation of fluorescent diretinal compounds, including pyridinium bisretinoid (A2E) and retinaldehyde dimer (RALdi).

The cytotoxicity of A2E, its derivatives, and RALdi is well established. These retinaldehyde adducts sensitize retinal pigment epithelium (RPE) cells to blue-light damage, impair the degradation of phospholipids from the phagocytosed rod outer segments, induce the release of pro-apoptotic proteins from the mitochondria, and destabilize cellular membranes. Further, oxidized A2E induces DNA fragmentation by forming adducts with purines and pyrimidines. Consequently, the accumulation of aberrant retinal metabolites, indicated by fundus autofluorescence, precedes macular degeneration and visual loss in Stargardt and AMD patients.

Retinaldehyde toxicity and intracellular deposits of its metabolites are the prominent features of malfunctioning visual cycle and aging RPE that contribute to chronic retinal diseases. Thus, regulating the the flux of retinoids can potentially provide a therapeutic approach to treating chronic retinal diseases. Multiple binding and transport proteins facilitate retinoid biology including cellular retinol-binding proteins (CRBPs). The major retinol-binding protein in RPE cells, CRBP1, enhances intracellular vitamin A uptake. The role of CRBP1 in the retinal pigmented epithelium (RPE) is particularly important since this carrier protein facilitates the recycling of vitamin A from the photoreceptor cells. Studies on CRBP1-deficient mice ($Rbp1^{-/-}$) revealed a diminished amount of all-trans-retinyl esters (atRE) in RPE and the transient accumulation of atROL upon recovery from exposure to bright light. This phenomenon was accompanied by delayed dark adaptation by a factor of two as compared to WT mice. Importantly, the deactivation of the Rbp1 gene does not cause pathological changes in the murine retina. Also, mutations in CRBP1 have not been reported in human retinal disorders.

Outside of the eye, CRBP1 mediates biosynthesis of another important bioactive metabolite of vitamin A, retinoic acid. CRBP1 binds all-trans-retinaldehyde and delivers this substrate to retinaldehyde dehydrogenases for biosynthesis of retinoic acid. Thus, antagonists of CRBP1 have potential to inhibit production of retinoic acid in selected tissues, including dendritic cells of mammalian immune system.

In addition to the regulation of vitamin A metabolism, members of the CRBP protein family are involved in maintaining a non-retinoid lipid homeostasis in vivo. Zizola C. F. et al. Am J Physiol Endocrinol Metab. 295, E1358-E1368, 2008. Deficiency of CRBP3 in mice is associated with reduced food intake, increased energy expenditure, and altered body composition with a decrease in adiposity and an increase in lean body mass. Moreover, when maintained on the high-fat diet, the lack of CRBP3 prevented mice form developing hepatic steatosis.

SUMMARY

Embodiments described herein relate to compounds that can be used as antagonists or inhibitors of cellular retinoid bind proteins (CRBPs) and, more particularly, to compounds and methods that can be used as antogonists or inibitors of CRB1, CRBP3, and/or CRBP4 and their use in treating (i) ocular and/or retinal disorders associated with aberrant all-trans-retinaldehyde (atRAL) clearance and/or formation of retinaldehyde metabolites in the retina, (ii) inflammatory and/or immune disorders associated with or affected by retinoic acid production, as well as (iii) metabolic disorders, obesity, and/or obesity-related conditions related to the physiological function of CRBP3 and/or CRBP4 in a subject in need thereof.

In some embodiments, the compounds can have a structure of formula (I):

(I)

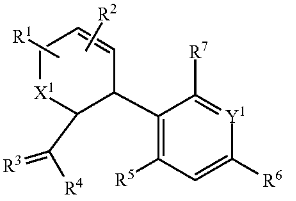

or a pharmaceutically acceptable salt, tautomer, or solvate thereof, wherein:

$R^1$ and $R^2$ are each independently H, halogen, alkyl, alkylene-alkoxy, hydroxyl, —C(O)-alkyl, or —C(O)O-alkyl, each of which is optionally substituted with $R^1$;

$R^3$ is alkyl, alkylene, or OH, each of which is optionally substituted with $R^1$;

$R^4$ is H, halogen, or alkyl, each of which is optionally substituted with $R^1$;

$R^5$ and $R^6$ are each independently hydroxyl, carboxyl, —C(O)-alkyl, —C(O)O— alkyl, alkylene-C(O)-alkyl, alkylene-C(O)O-alkyl, $N(R^9)_2$, alkylene-$NH_2$, alkylene-$N(R^9)_2$, or —$N(R^8)$(alkylene-OH), each of which is optionally substituted with $R^8$;

$R^7$ is H, halogen, hydroxyl, carboxyl, —C(O)-alkyl, —C(O)O-alkyl, alkyl, alkylene-C(O)-alkyl, alkylene-C(O)O-alkyl, $N(R^9)_2$, alkylene-$NH_2$, alkylene-$N(R^9)_2$, alkylene-OH, or —$N(R^9)$(alkylene-OH), each of which is optionally substituted with $R^1$;

$R^8$ is halogen, alkyl, haloalkyl, alkoxy, or haloalkoxy;

$R^9$ is H, halogen, alkyl, haloalkyl, alkoxy, or haloalkoxy;

$X^1$ is NH, O, or $CH_2$;

$Y^1$ is N or CH; and the dashed line is an optional bond.

In some embodiments, $R^1$ is H, $C_1$-$C_6$ alkyl, or $C_1$-$C_6$ haloalkyl.

In other embodiments, $R^2$ is $C_1$-$C_6$ alkyl, or $C_1$-$C_6$ haloalkyl.

In still other embodiments, $R^3$ is methyl, ethyl, propyl, methylene, ethylene, propylene, or OH.

In some embodiments, $R^4$ is H, methyl, ethyl, or propyl.

In other embodiments, $R^5$ and $R^6$ are each independently hydroxyl, carboxyl, —C(O)-alkyl, —C(O)O-alkyl, alkylene-C(O)-alkyl, alkylene-C(O)O-alkyl, or $N(R^9)_2$.

In still other embodiments, $R^7$ is H, halogen, hydroxyl, carboxyl, $C_1$-$C_6$ alkyl, —C(O)—($C_1$-$C_6$ alkyl), —C(O)O—($C_1$-$C_6$ alkyl), —($C_1$-$C_6$ alkylene)-C(O)—($C_1$-$C_6$ alkyl), —($C_1$-$C_6$ alkylene)-C(O)O—($C_1$-$C_6$ alkyl), $N(R^9)_2$, —($C_1$-$C_6$ alkylene)-$NH_2$, —($C_1$-$C_6$ alkylene)-$N(R^9)_2$, —($C_1$-$C_6$ alkylene)-OH, or —$N(R^9)$(—($C_1$-$C_6$ alkylene)-OH), for example, $R^7$ can be H, halogen, hydroxyl, carboxyl, or $C_1$-$C_6$ alkyl In some embodiments, the compound can be a selective CRBP1 antagonist. In other embodiments, the compound can be a selective CRBP3 or CRBP4 antagonist. The CRBP antagonist or compound does not produce psychoactive effects in the subject, bind to and/or interact with cannabinoid receptor 1 and/or 2, inhibit enzymatic activities of enzymes involved in the regeneration of visual chromophores, and/or inhibit enzymatic activities of enzymes involved in the production of retinoic acid or its geometric isomers.

In other embodiments, the compound can lower the concentration of retinaldehyde in retinal tissues, reduce the formation of A2E and/or retinal dimer in the subject's retina, and/or inhibit bright light-induced retinal damage in a $Rdh8^{-/-}Abca4^{-/-}$ mouse.

In some embodiments, the compound can be delivered to the subject by at least one of topical administration, systemic administration, intravitreal injection, and intraocular delivery.

In other embodiments, the compound can be provided in an ocular preparation for sustained delivery.

In other embodiments, the ocular disorder treated by the compound can include at least one of light induced retinal degeneration, macular degeneration, Stargardt's disease, geographic atrophy, retinitis pigmentosa, Leber's congenital amaurorsis, and cone-rod dystrophy.

In other embodiments, the inflammatory and/or immune disorder associated with or affected by retinoic acid production in a subject, which can be treated by the compounds, can include at least one of achlorhydra autoimmune active chronic hepatitis, acute disseminated encephalomyelitis, acute hemorrhagic leukoencephalitis, Addison's disease, agammaglobulinemia, alopecia areata, Alzheimer's disease, amyotrophic lateral sclerosis, ankylosing spondylitis, anti-gbm/tbm nephritis, antiphospholipid syndrome, antisynthetase syndrome, aplastic anemia, arthritis, atopic allergy, atopic dermatitis, autoimmune cardiomyopathy, autoimmune hemolytic anemia, autoimmune hepatitis, autoimmune inner ear disease, autoimmune lymphoproliferative syndrome, autoimmune peripheral neuropathy, autoimmune polyendocrine syndrome, autoimmune progesterone dermatitis, autoimmune thrombocytopenia purpura, autoimmune uveitis, balo disease/balo concentric sclerosis, Bechets syndrome, Berger's disease, Bickerstaff's encephalitis, Blau syndrome, bullous pemphigoid, Castleman's disease, Chagas disease, chronic fatigue immune dysfunction syndrome, chronic inflammatory demyelinating polyneuropathy, chronic lyme disease, chronic obstructive pulmonary disease, Churg-Strauss syndrome, cicatricial pemphigoid, coeliac disease, Cogan syndrome, cold agglutinin disease, cranial arteritis, crest syndrome, Crohns disease, Cushing's syndrome, Dego's disease, Dercum's disease, dermatitis herpetiformis, dermatomyositis, diabetes mellitus type 1, Dressler's syndrome, discoid lupus erythematosus, eczema, endometriosis, enthesitis-related arthritis, eosinophilic fasciitis, epidermolysis bullosa acquisita, essential mixed cryoglobulinemia, Evan's syndrome, fibrodysplasia ossificans progressive, fibromyalgia, fibromyositis, fibrosing aveolitis, gastritis, gastrointestinal pemphigoid, giant cell arteritis, glomerulonephritis, Goodpasture's syndrome, Graves' disease, Guillain-barré syndrome (GBS), Hashimoto's encephalitis, Hashimoto's thyroiditis, henoch-schonlein purpura, hidradenitis suppurativa, Hughes syndrome, inflammatory bowel disease (IBD), idiopathic inflammatory demyelinating diseases, idiopathic pulmonary fibrosis, idiopathic thrombocytopenic purpura, iga nephropathy, inflammatory demyelinating polyneuopathy, interstitial cystitis, irritable bowel syndrome (IBS), Kawasaki's disease, lichen planus, Lou Gehrig's disease, lupoid hepatitis, lupus erythematosus, ménière's disease, microscopic polyangiitis, mixed connective tissue disease, morphea, multiple myelema, multiple sclerosis, myasthenia gravis, myositis, narcolepsy, neuromyelitis optica, neuromyotonia, occular cicatricial pemphigoid, opsoclonus myoclonus syndrome, ord thyroiditis, Parkinson's disease, pars planitis, pemphigus, pemphigus vulgaris, pernicious anaemia, polymyalgia rheumatic, polymyositis, primary biliary cirrhosis, primary sclerosing cholangitis, progressive inflammatory neuropathy, psoriasis, psoriatic arthritis, raynaud phenomenon, relapsing polychondritis, Reiter's syndrome, rheumatoid arthritis, rheumatoid fever, sarcoidosis, schizophrenia, Schmidt syndrome, Schnitzler syndrome, scleritis, scleroderma, Sjøgren's syndrome, spondyloarthropathy, sticky blood syndrome, still's disease, stiff person syndrome, sydenham chorea, sweet syndrome, takayasu's arteritis, temporal arteritis, transverse myelitis, ulcerative colitis, undifferentiated connective tissue disease, undifferentiated spondyloarthropathy, vasculitis, vitiligo, Wegener's granulomatosis, Wilson's syndrome, Wiskott-Aldrich syndrome, hypersensitivity reactions of the skin, atherosclerosis, ischemia-reperfusion injury, myocardial infarction, and restenosis, fulminating or disseminated pulmonary tuberculosis when used concurrently with appropriate chemotherapy, hypersensitivity pneumonitis, idiopathic bronchiolitis obliterans with organizing pneumonia, idiopathic eosinophilic pneumonias, idiopathic pulmonary fibrosis, *Pneumocystis carinii* pneumonia (PCP) associated with hypoxemia occurring in an HIV(+) individual who is also under treatment with appropriate anti-PCP antibiotics, a diuresis or remission of proteinuria in nephrotic syndrome, without uremia, of the idiopathic type or that due to lupus erythematosus, ankylosing spondylitis, polymyalgia rheumatic, psoriatic arthritis, relapsing polychondritis, trichinosis with neurologic or myocardial involvement, and tuberculous meningitis.

In still other embodiments, the inflammatory and/or immune disorder can include at least one of oral ulcers, gum disease, gastritis, colitis, ulcerative colitis, gastric ulcers, inflammatory bowel disease, and Crohn's disease.

In other embodiments, the metabolic disorders associated with dysregulation of lipid homeostasis in a subject, which can be treated by the compounds, can include at least one of obesity, obesity-related conditions, dyslipidemia, non-alcoholic fatty liver disease, liver steatosis, or metabolic syndrome.

DETAILED DESCRIPTION

Figure 1:
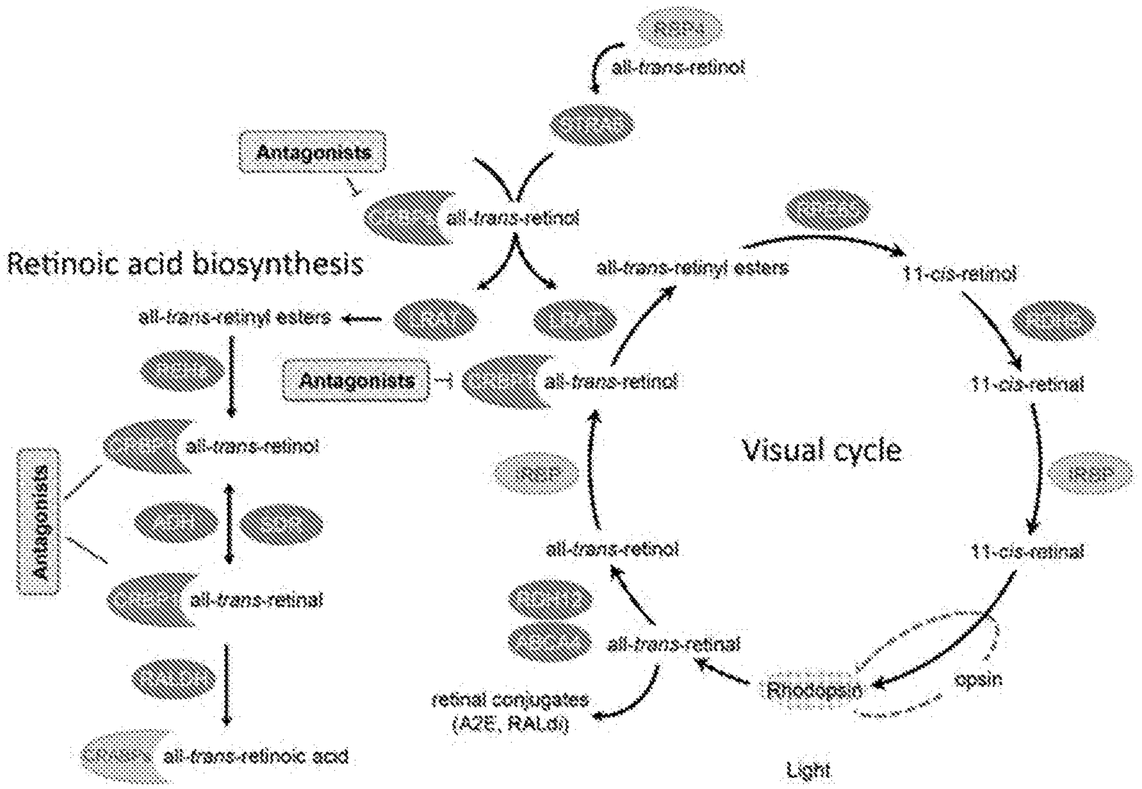
FIG. 1 illustrates a schematic showing uptake of vitamin A and the synthesis of visual chromophore and retinoic acid.

While the following terms are believed to be well understood by one of ordinary skill in the art, the following definitions are set forth to facilitate explanation of the presently disclosed subject matter.

As used herein, the verb "comprise" as is used in this description and in the claims and its conjugations are used in its non-limiting sense to mean that items following the word are included, but items not specifically mentioned are not excluded. The present invention may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The term "pharmaceutically acceptable" means suitable for use in contact with the tissues of humans and animals without undue toxicity, irritation, allergic response, and the like, commensurate with a reasonable benefit/risk ratio, and effective for their intended use within the scope of sound medical judgment.

The term "pharmaceutically acceptable salts" include those obtained by reacting the active compound functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. Those skilled in the art will further recognize that acid addition salts may be prepared by reaction of the compounds with the appropriate inorganic or organic acid via any of a number of known methods. The term "pharmaceutically acceptable salts" also includes those obtained by reacting the active compound functioning as an acid, with an inorganic or organic base to form a salt, for example salts of ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris-(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, and the like. Non-limiting examples of inorganic or metal salts include lithium, sodium, calcium, potassium, magnesium salts and the like.

Additionally, the salts of the compounds described herein, can exist in either hydrated or unhydrated (the anhydrous) form or as solvates with other solvent molecules. Non-limiting examples of hydrates include monohydrates, dihydrates, etc. Non-limiting examples of solvates include ethanol solvates, acetone solvates, etc.

The term "solvates" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The term "isomerism" refers to compounds that have identical molecular formulae, but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

The term "chiral isomer" refers to a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has 2n-1 enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al, Angew. Chem. Inter. Edit. 1966, 5, 385; errata 511; Cahn et al., Angew. Chem. 1966, 78, 413; Cahn and Ingold, J Chem. Soc. 1951 (London), 612; Cahn et al., Experientia 1956, 12, 81; Cahn, J., Chem. Educ. 1964, 41, 116).

The term "geometric isomers" refer to the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Further, the structures and other compounds discussed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The compounds and salts described herein can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

The terms below, as used herein, have the following meanings, unless indicated otherwise:

"Amino" refers to the $-NH_2$ radical.

"Cyano" refers to the —CN radical.

"Halo" or "halogen" refers to bromo, chloro, fluoro or iodo radical.

"Hydroxy" or "hydroxyl" refers to the —OH radical.

"Imino" refers to the =NH substituent.

"Nitro" refers to the $=NO_2$ radical.

"Oxo" refers to the =O substituent.

"Thioxo" refers to the =S substituent.

"Alkyl" or "alkyl group" refers to a fully saturated, straight or branched hydrocarbon chain radical having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

"Alkylene" or "alkylene chain" refers to a fully saturated, straight or branched divalent hydrocarbon chain radical, and having from one to twelve carbon atoms. Non-limiting examples of $C_1$-$C_{12}$ alkylene include methylene, ethylene, propylene, n-butylene, ethenylene, propenylene, n-butenylene, propynylene, n-butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, an alkylene chain can be optionally substituted.

"Alkenyl" or "alkenyl group" refers to a straight or branched hydrocarbon chain radical having from two to twelve carbon atoms, and having one or more carbon-carbon double bonds. Each alkenyl group is attached to the rest of the molecule by a single bond. Alkenyl group comprising any number of carbon atoms from 2 to 12 are included. An alkenyl group comprising up to 12 carbon atoms is a $C_2$-$C_{12}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes $C_{11}$ and $C_{12}$ alkenyls. Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Unless stated otherwise specifically in the specification, an alkyl group can be optionally substituted.

"Alkenylene" or "alkenylene chain" refers to a straight or branched divalent hydrocarbon chain radical, having from two to twelve carbon atoms, and having one or more carbon-carbon double bonds. Non-limiting examples of $C_2$-$C_{12}$ alkenylene include ethene, propene, butene, and the like. The alkenylene chain is attached to the rest of the molecule through a single bond and to the radical group through a single bond. The points of attachment of the alkenylene chain to the rest of the molecule and to the radical group can be through one carbon or any two carbons within the chain. Unless stated otherwise specifically in the specification, an alkenylene chain can be optionally substituted.

"Alkynyl" or "alkynyl group" refers to a straight or branched hydrocarbon chain radical having from two to twelve carbon atoms, and having one or more carbon-carbon triple bonds. Each alkynyl group is attached to the rest of the molecule by a single bond. Alkynyl group comprising any number of carbon atoms from 2 to 12 are included. An alkynyl group comprising up to 12 carbon atoms is a $C_2$-$C_{12}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls. Non-limiting examples of $C_2$-$C_{12}$ alkenyl include ethynyl, propynyl, butynyl, pentynyl and the like. Unless stated otherwise specifically in the specification, an alkyl group can be optionally substituted.

"Alkynylene" or "alkynylene chain" refers to a straight or branched divalent hydrocarbon chain radical, having from two to twelve carbon atoms, and having one or more carbon-carbon triple bonds. Non-limiting examples of $C_2$-$C_{12}$ alkynylene include ethynylene, propargylene and the like. The alkynylene chain is attached to the rest of the molecule through a single bond and to the radical group through a single bond. The points of attachment of the alkynylene chain to the rest of the molecule and to the radical group can be through one carbon or any two carbons within the chain. Unless stated otherwise specifically in the specification, an alkynylene chain can be optionally substituted.

"Alkoxy" refers to a radical of the formula —ORa where $R_a$ is an alkyl, alkenyl or alknyl radical as defined above containing one to twelve carbon atoms. Unless stated otherwise specifically in the specification, an alkoxy group can be optionally substituted.

"Alkylamino" refers to a radical of the formula $—NHR_a$ or $—NR_aR_a$ where each $R_a$is, independently, an alkyl, alkenyl or alkynyl radical as defined above containing one to twelve carbon atoms. Unless stated otherwise specifically in the specification, an alkylamino group can be optionally substituted.

"Alkylcarbonyl" refers to the $—C(=O)R_a$ moiety, wherein $R_a$ is an alkyl, alkenyl or alkynyl radical as defined above. A non-limiting example of an alkyl carbonyl is the methyl carbonyl ("acetal") moiety. Alkylcarbonyl groups can also be referred to as "$C_w$-$C_z$ acyl" where w and z depicts the range of the number of carbon in $R_a$, as defined above. For example, "$C_1$-$C_{10}$ acyl" refers to alkylcarbonyl group as defined above, where $R_a$ is $C_1$-$C_{10}$ alkyl, $C_2$-$C_{10}$ alkenyl, or $C_2$-$C_{10}$ alkynyl radical as defined above. Unless stated otherwise specifically in the specification, an alkyl carbonyl group can be optionally substituted.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group can be optionally substituted.

"Haloalkenyl" refers to an alkenyl radical, as defined above, that is substituted by one or more halo radicals, as defined above, e.g., 1-fluoropropenyl, 1,1-difluorobutenyl, and the like. Unless stated otherwise specifically in the specification, a haloalkenyl group can be optionally substituted.

"Haloalkynyl" refers to an alkynyl radical, as defined above, that is substituted by one or more halo radicals, as defined above, e.g., 1-fluoropropynyl, 1-fluorobutynyl, and the like. Unless stated otherwise specifically in the specification, a haloalkynyl group can be optionally substituted.

The term "substituted" used herein means any of the above groups (e.g., alkyl, alkylene, alkenyl, alkenylene, alkynyl, alkynylene, alkoxy, alkylamino, alkylcarbonyl, thioalkyl, aryl, aralkyl, carbocyclyl, cycloalkyl, cycloalkenyl, cycloalkynyl, cycloalkylalkyl, haloalkyl, heterocyclyl, N-heterocyclyl, heterocyclylalkyl, heteroaryl, N-heteroaryl, heteroarylalkyl, heteroarylalkenyl, heteroarylalkynyl, etc) wherein at least one hydrogen atom is replaced by a bond to a non-hydrogen atoms such as, but not limited to: a halogen atom such as F, Cl, Br, and I; an oxygen atom in groups, such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with:

$-NR_gR_h$, $-NR_gC(=O)R_h$, $-NR_gC(=O)NR_gR_h$, $-NR_gC(=O)OR_h$, $-NR_gSO_2R_h$, $-OC(=O)NR_gR_h$, $-OR_g$, $-SR_g$, $-SOR_g$, $-SOZR_g$, $-OSOaR_g$, $-SO_ZOR_g$, $=NSOaR_g$, and $-SO_2NR_gR_h$. "Substituted" also means any of the above groups in which one or more hydrogen atoms are replaced with $-C(=O)R_g$, $-C(=O)OR_g$, $-C(=O)NR_gR_h$, $-CH_2SO_2R_g$, $-CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrastemal injection and infusion.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" is art-recognized and includes stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

A "patient," "subject," or "host" to be treated by the subject method may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder.

The terms "prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

When an atom or a chemical moiety is followed by a subscripted numeric range (e.g., $C_{1-6}$), the invention is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

All percentages and ratios used herein, unless otherwise indicated, are by weight.

The term "retina" refers to a region of the central nervous system with approximately 150 million neurons. It is located at the back of the eye where it rests upon a specialized epithelial tissue called retinal pigment epithelium or RPE. The retina initiates the first stage of visual processing by transducing visual stimuli in specialized neurons called "photoreceptors". Their synaptic outputs are processed by elaborate neural networks in the retina and then transmitted to the brain. The retina has evolved two specialized classes of photoreceptors to operate under a wide range of light conditions. "Rod" photoreceptors transduce visual images under low light conditions and mediate achromatic vision. "Cone" photoreceptors transduce visual images in dim to bright light conditions and mediate both color vision and high acuity vision.

Every photoreceptor is compartmentalized into two regions called the "outer" and "inner" segment. The inner segment is the neuronal cell body containing the cell nucleus. The inner segment survives for a lifetime in the absence of retinal disease. The outer segment is the region where the light sensitive visual pigment molecules are concentrated in a dense array of stacked membrane structures. Part of the outer segment is routinely shed and regrown in a diurnal process called outer segment renewal. Shed outer segments are ingested and metabolized by RPE cells.

The term "macula" refers to the central region of the retina, which contains the fovea where visual images are processed by long slender cones in high spatial detail ("visual acuity"). "Macular degeneration" is a form of retinal neurodegeneration, which attacks the macula and destroys high acuity vision in the center of the visual field. AMD can be in a "dry form" characterized by residual lysosomal granules called lipofuscin in RPE cells, and by extracellular deposits called "drusen". Drusen contain cellular waste products excreted by RPE cells. "Lipofuscin" and drusen can be detected clinically by ophthalmologists and quantified using fluorescence techniques. They can be the first clinical signs of macular degeneration.

Lipfuscin contains aggregations of A2E. Lipofuscin accumulates in RPE cells and poisons them by multiple known mechanisms. As RPE cells become poisoned, their biochemical activities decline and photoreceptors begin to degenerate. Extracellular drusen may further compromise RPE cells by interfering with their supply of vascular nutrients. Drusen also trigger inflammatory processes, which leads to choroidal neovascular invasions of the macula in one patient in ten who progresses to wet form AMD. Both the dry form and wet form progress to blindness.

The term "ERG" is an acronym for electroretinogram, which is the measurement of the electric field potential emitted by retinal neurons during their response to an experimentally defined light stimulus. ERG is a non-invasive measurement, which can be performed on either living subjects (human or animal) or a hemisected eye in solution that has been removed surgically from a living animal.

The term "metabolic disorders" refers to a group of identified disorders in which errors of metabolism, imbalances in metabolism, or sub-optimal metabolism occur. The metabolic disorders as described herein also include diseases that can be treated through the modulation of metabolism, although the disease itself may or may not be caused by a specific metabolic defect. Such metabolic disorders may involve, for example, glucose oxidation pathways.

The term "obesity" as used herein is defined in the WHO classifications of weight. Underweight is less than 18.5 BMI (thin); healthy is 18.5-24.9 BMI (normal); grade 1 overweight is 25.0-29.9 BMI (overweight); grade 2 overweight is 30.0-39.0 BMI (obesity); grade 3 overweight is greater than or equal to 40.0 BMI. BMI is body mass index (morbid obesity) and is $kg/m^2$. Waist circumference can also be used to indicate a risk of metabolic complications. Waist circumference can be measured (in cm) at midpoint between the lower border of ribs and the upper border of the pelvis. Other measures of obesity include, but are not limited to, skinfold thickness and bioimpedance, which is based on the principle that lean mass conducts current better than fat mass because it is primarily an electrolyte solution.

The term "obesity-related condition" refers to any disease or condition that is caused by or associated with (e.g., by biochemical or molecular association) obesity or that is caused by or associated with weight gain and/or related biological processes that precede clinical obesity. Examples of obesity-related conditions include, but are not limited to, type 2 diabetes, metabolic syndrome (i.e., Syndrome X), hyperglycemia, hyperinsulinemia, impaired glucose tolerance, impaired fasting glucose, dyslipidemia, hypertriglyceridemia, insulin resistance, hypercholesterolemia, atherosclerosis, coronary artery disease, peripheral vascular disease, and hypertension.

The term "metabolic syndrome" refers a combination of medical disorders that increase one's risk for cardiovascular disease and diabetes. It is known under various other names, such as (metabolic) syndrome X, insulin resistance syndrome, Reaven's syndrome. Symptoms and features are fasting hyperglycemia, diabetes mellitus type 2 or impaired fasting glucose, impaired glucose tolerance, or insulin resistance; high blood pressure; central obesity (also known as visceral, male-pattern or apple-shaped adiposity), overweight with fat deposits mainly around the waist; decreased HDL cholesterol; elevated triglycerides; and elevated uric acid levels. Associated diseases and signs are: fatty liver (especially in concurrent obesity), progressing to non-alcoholic fatty liver disease, polycystic ovarian syndrome, hemochromatosis (iron overload); and acanthosis nigricans (a skin condition featuring dark patches).

Embodiments described herein relate to compounds that can be used as antagonists or inhibitors of cellular retinoid bind proteins (CRBPs) and, more particularly, to compounds and methods that can be used as antogonists or inibitors of CRB1, CRBP3, and/or CRBP4 and their use in treating (i) ocular and/or retinal disorders associated with aberrant all-trans-retinaldehyde (atRAL) clearance and/or formation of retinaldehyde metabolites in the retina, (ii) inflammatory and/or immune disorders associated with or affected by retinoic acid production, as well as (iii) metabolic disorders, obesity, and/or obesity-related conditions related to the physiological function of CRBP3 and/or CRBP4 in a subject in need thereof.

It was discovered that abnormal cannabidiol (abn-CBD) is a non-retinoid ligand of selected cellular retinol binding proteins CRBPs, such as CRBP1, CRBP3, and CRBP4 (FIGS. 5 and 9). This non-psychoactive derivative of cannabidiol exerts its biological activity by competing with all-trans retinol (atROL) for the binding site of CRBPs at pharmacologically relevant concentrations (FIG. 3) and can serve as a pharmacological tool to influence vitamin A metabolism in vivo.

Figure 7A:
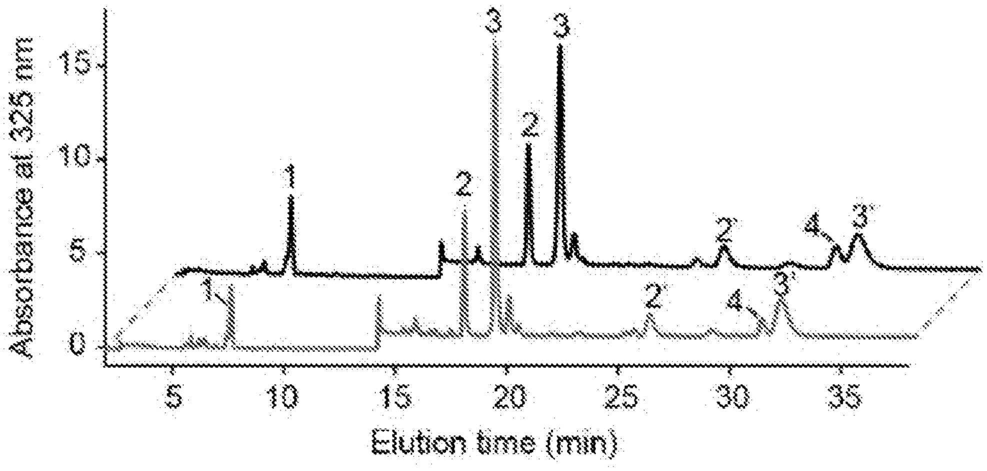
FIGS. 7(A-C) illustrate plots showing the effect of abn-CBD on the temporal retinoid composition upon regeneration of the visual chromophore. (A) HPLC separation of retinoids extracted from a mouse eye 1 h after exposure to light (grey and black traces represent control and abn-CBD-treated samples, respectively). Peak 1-all-trans-retinyl esters (atRE), 2,2'-11-cis-retinaldehdye oxime (syn and anti, respectively) (11cRAL), 3,3'-all-trans-retinaldehyde oxime (syn, anti, respectively) (atRAL), 4-all-trans-retinol (atROL). (B) Quantification of visual cycle retinoid during recovery from the light stimulus. Black bars correspond to data obtained for control (DMSO-treated) mice, where gray bars represent samples from animals administrated with abn-CBD. The bars represent the mean values±sd (n=4). (C) Single-flash ERG responses of increasing light intensity for abn-CBD-treated mice. ERG responses were recorded in mice 4 h after a flash of light that bleached ~40% of their visual pigment. ERG data represent the means and s.d. of both a-wave and b-wave amplitudes (n=8). Mice were administrated with a single dose of abn-CBD (30 mg kg-1) 1 h before exposure to light. Systemic administration of abn-CBD (○) caused slight delay in the dark adaptation as compared to the vehicle treated animal (•). Two-factor ANOVA test for treated and control groups of mice revealed p-values of 0.002 and 0.035 for a- and bwaves amplitudes, respectively. The asterisks depict significance: *p<0.02 as determined by equal variance t-test between groups with the same light stimulus.
Figure 7B:
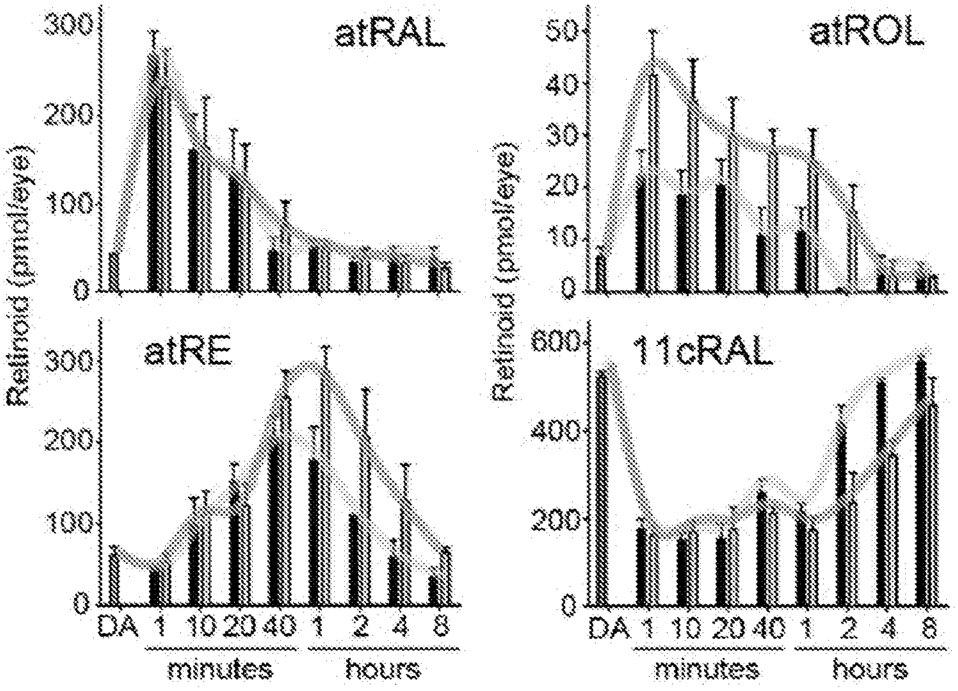

Advantageously, it was found that abn-CBD can affect the flux of retinoids via the visual cycle during the regeneration of visual chromophore after light exposure. The administration of abn-CBD can affect the transport of atROL between the photoreceptor and RPE cells and its esterification, which in turn can result in moderately delayed regeneration of visual chromophore. Importantly, the impaired flow of retinoids between these two cell types did not result in impaired clearance of retinaldehyde (FIG. 7). Although the conversion of retinol to retinal is at equilibrium in the two-cell system, atROL seems to be rapidly removed from the photoreceptor outer segments by partitioning into the interphotoreceptor matrix, where it is sequestered by interphotoreceptor retinoid-binding protein. Thus, atROL does not persist in the photoreceptor cells, preventing its mass action-driven oxidation back to retinaldehyde.

Limiting the rate of visual chromophore regeneration can avert light-induced retinal degeneration and lessen the accumulation of cytotoxic retinaldehyde metabolites. abn-CBD and non-psychoactive analogues thereof were found to prevent acute light-induced retinal damage in Balb/cJ mice (FIG. 7). A single dose of abn-CBD was sufficient to alter retinoid metabolism for long enough to provide protection against a light stimulus that in untreated animals caused irreversible retinal degeneration. This favorable effect relates to the fact that during light illumination the vast majority of visual chromophore is produced from recycled all-trans-retinaldehyde within the photoreceptor and RPE cells rather than synthesized from vitamin A newly acquired from bloodstream.

Additionally, abn-CBD does not interact with enterocyte-specific CRBP2. This protein is exclusively expressed in enterocytes in the small intestine, where it mediates the uptake of dietary vitamin A. The inhibition of CRBP2 could impair the efficient absorption of vitamin A as evidenced by the phenotype of $Rbp2^{-/-}$ mice. Thus, the lack of toxicity and inability to interfere with CRBP2 activity make abn-CBD suitable for the long-term treatment of progressive retinal degenerative diseases.

Accordingly, compounds having the structure of abn-CBD and/or analogues thereof can be used as inhibitors or antagonists of CRBP and be used in the treatment of and/or prevention ocular and/or retinal disorders associated with aberrant all-trans-retinaldehyde clearance and/or formation of retinaldehyde metabolites in the retina, treatment and/or prevention of inflammatory and/or immune disorders associated with or affected by retinoic acid production, as well as metabolic disorders, obesity, or obesity-related conditions related to the physiological function of CRBP3 and/or CRBP4 in a subject in need thereof.

In some embodiments, the compounds can be a selective CRBP1 antagonist. By selective CRBP antagonist it is meant the compound binds to one CRPB (e.g., CRPB1) at a higher affinity than other CRBPs (e.g., CRBP2) and/or binds to one CRPB (e.g., CRPB1), but does not bind to other CRPBs (e.g., CRBP2). For example, the compound can be a selective CRBP1 antagonist. The selective CRBP1 antagonist can bind to CRPB1 at a higher affinity than CRBP2, CRBP3, and/or CRBP4, and/or bind to CRPB1 but not CRBP2, CRBP3, and/or CRBP4. In another example, the compound can be a selective CRBP3 and CRBP4 antagonist. The selective CRBP3 and CRBP4 antagonist can bind to CRBP3 and CRBP4 at a higher affinity than CRPB1 and/or CRBP2 and/or bind to CRBP3 and CRBP4, but not CRBP1 and/or CRBP2.

In other embodiments, the compounds do not produce psychoactive effects in the subject, bind to and/or interact with cannabinoid receptor 1 and/or 2, inhibit enzymatic activities of enzymes involved in the regeneration of visual chromophores, and/or inhibit enzymatic activities of enzymes involved in the production of retinoic acid or its geometric isomers.

In some embodiments, the compound can have a structure of formula (I):

(I)

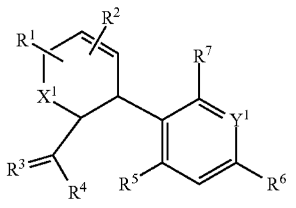

or a pharmaceutically acceptable salt, tautomer, or solvate thereof, wherein:

$R^1$ and $R^2$ are each independently H, halogen, alkyl, alkylene-alkoxy, hydroxyl, —C(O)-alkyl, or —C(O)O-alkyl, each of which is optionally substituted with $R^8$;

$R^3$ is alkyl, alkylene, or OH, each of which is optionally substituted with $R^8$;

$R^4$ is H, halogen, or alkyl, each of which is optionally substituted with $R^8$;

$R^5$ and $R^6$ are each independently hydroxyl, carboxyl, —C(O)-alkyl, —C(O)O— alkyl, alkylene-C(O)-alkyl, alkylene-C(O)O-alkyl, $N(R^9)_2$, alkylene-$NH_2$, alkylene-$N(R^9)_2$, or —$N(R^9)$(alkylene-OH), each of which is optionally substituted with $R^8$;

$R^7$ is H, halogen, hydroxyl, carboxyl, —C(O)-alkyl, —C(O)O-alkyl, alkyl, alkylene-C(O)-alkyl, alkylene-C(O)O-alkyl, $N(R^9)_2$, alkylene-$NH_2$, alkylene-$N(R^9)_2$, alkylene-OH, or —$N(R^9)$(alkylene-OH), each of which is optionally substituted with $R^8$;

$R^8$ is halogen, alkyl, haloalkyl, alkoxy, or haloalkoxy;

$R^9$ is H, halogen, alkyl, haloalkyl, alkoxy, or haloalkoxy;

$X^1$ is NH, O, or $CH_2$;

$Y^1$ is N or CH; and the dashed line is an optional bond.

In some embodiments, $R^1$ is H, $C_1$-$C_6$ alkyl, or $C_1$-$C_6$ haloalkyl.

In other embodiments, $R^2$ is $C_1$-$C_6$ alkyl, or $C_1$-$C_6$ haloalkyl.

In still other embodiments, $R^3$ is methyl, ethyl, propyl, methylene, ethylene, propylene, or OH.

In some embodiments, $R^4$ is H, methyl, ethyl, or propyl.

In other embodiments, $R^5$ and $R^6$ are each independently hydroxyl, carboxyl, —C(O)-alkyl, —C(O)O-alkyl, alkylene-C(O)-alkyl, alkylene-C(O)O-alkyl, or $N(R^9)_2$.

In still other embodiments, $R^7$ is H, halogen, hydroxyl, carboxyl, $C_1$-$C_6$ alkyl, —C(O)—($C_1$-$C_6$ alkyl), —C(O)O—($C_1$-$C_6$ alkyl), —($C_1$-$C_6$ alkylene)-C(O)—($C_1$-$C_6$ alkyl), —($C_1$-$C_6$ alkylene)-C(O)O—($C_1$-$C_6$ alkyl), $N(R^9)_2$, —($C_1$-$C_6$ alkylene)-$NH_2$, —($C_1$-$C_6$ alkylene)-$N(R^9)_2$, —($C_1$-$C_6$ alkylene)-OH, or —$N(R^9)$(—($C_1$-$C_6$ alkylene)-OH), for example, $R^7$ can be H, halogen, hydroxyl, carboxyl, or $C_1$-$C_6$ alkyl.

In other embodiments, the compound can have a structure of formula (II):

(II)

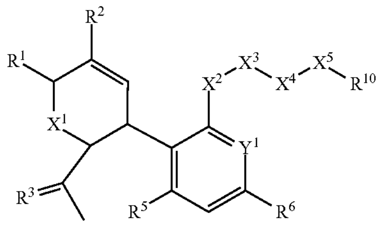

or a pharmaceutically acceptable salt, tautomer, or solvate thereof, wherein:

$R^1$ and $R^2$ are each independently H, halogen, alkyl, alkylene-alkoxy, hydroxyl, —C(O)-alkyl, or —C(O)O-alkyl, each of which is optionally substituted with $R^1$;

$R^3$ is alkyl, alkylene, or OH, each of which is optionally substituted with $R^8$;

$R^5$ and $R^6$ are each independently hydroxyl, carboxyl, —C(O)-alkyl, —C(O)O— alkyl, alkylene-C(O)-alkyl, alkylene-C(O)O-alkyl, $N(R^9)_2$, alkylene-$NH_2$, alkylene-$N(R^9)_2$, or —$N(R^9)$(alkylene-OH), each of which is optionally substituted with $R^1$;

$R^8$ is halogen, alkyl, haloalkyl, alkoxy, or haloalkoxy;

$R^9$ is H, halogen, alkyl, haloalkyl, alkoxy, or haloalkoxy;

$R^{10}$ is H, halogen, hydroxyl, carboxyl, —C(O)-alkyl, —C(O)O-alkyl, alkylene-C(O)-alkyl, alkylene-C(O)O-alkyl, $N(R^9)_2$, alkylene-$NH_2$, alkylene-$N(R^9)_2$, or —$N(R^9)$(alkylene-OH), each of which is optionally substituted with $R^1$; and $X^1$ is NH, O, or $CH_2$;

$X^2$, $X^3$, $X^4$, $X^5$ are independently NH, O, $CH_2$, or absent;

$Y^1$ is N or CH; and the dashed line is an optional bond.

In some embodiments, $R^1$ is H, $C_1$-$C_6$ alkyl, or $C_1$-$C_6$ haloalkyl, $R^2$ is $C_1$-$C_6$ alkyl, or $C_1$-$C_6$ haloalkyl, $R^3$ is methyl, ethyl, propyl, methylene, ethylene, propylene, or OH, $R^4$ is H, methyl, ethyl, or propyl, and $R^5$ and $R^6$ are each independently hydroxyl, carboxyl, —C(O)-alkyl, —C(O)O-alkyl, alkylene-C(O)-alkyl, or alkylene-C(O)O-alkyl, $N(R^9)_2$.

In other embodiments, the compound can have a structure of formula (III):

(III)

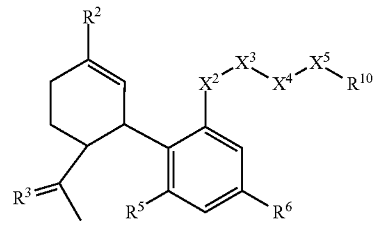

or a pharmaceutically acceptable salt, tautomer, or solvate thereof, wherein:

$R^2$ is $C_1$-$C_6$ alkyl, or $C_1$-$C_6$ haloalkyl;

$R^3$ is methyl, ethyl, propyl, methylene, ethylene, propylene, or OH;

$R^5$ and $R^6$ are each independently hydroxyl, carboxyl, —C(O)-alkyl, —C(O)O— alkyl, alkylene-C(O)-alkyl, alkylene-C(O)O-alkyl, or $N(R^9)_2$;

$R^8$ is halogen, alkyl, haloalkyl, alkoxy, or haloalkoxy;

$R^9$ is H, halogen, alkyl, haloalkyl, alkoxy, or haloalkoxy;

$R^{10}$ is H, halogen, hydroxyl, carboxyl, —C(O)-alkyl, —C(O)O-alkyl, alkylene-C(O)-alkyl, alkylene-C(O)O-alkyl, $N(R^9)_2$, alkylene-$NH_2$, alkylene-$N(R^9)_2$, or —$N(R^9)$(alkylene-OH), each of which is optionally substituted with $R^8$;

$X^2$, $X^3$, $X^4$, $X^5$ are independently NH, O, $CH_2$, or absent; and the dashed line is an optional bond.

In some embodiments, a compound having a structure of formula (I) can have a structure of formula (IV):

(IV)

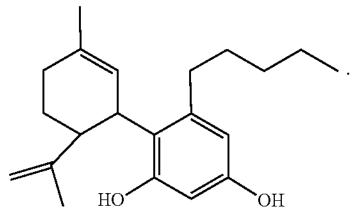

In other embodiments, a compound having a structure of formula (I) can have a structure of formula (V):

(V)

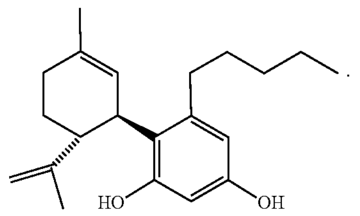

In other embodiments, a compound of formula (I) does not have a structure of formula (IV) or formula (V):

(IV)

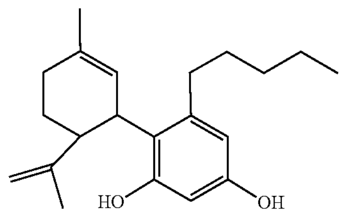

or (V)

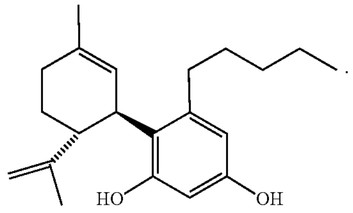

In some embodiments, a therapeutically effective amount of the CRBP antagonist or compounds described herein can be administered to a subject to treat (e.g., control, relieve, ameliorate, alleviate, or slow the progression of) and/or prevent (e.g., delay the onset of or reduce the risk of developing) ocular and/or retinal disorders associated with aberrant all-trans-retinaldehyde and/or formation of retinaldehyde metabolites in the retina. A therapeutically effectively amount of the CRBP antagonist administered to the subject can be an amount effective to lower the concentration of retinaldehyde in retinal tissues, reduce the formation of A2E and/or retinal dimer in the subject's retina, and/or inhibit bright light-induced retinal damage in a Rdh8$^{-/-}$-Abca4$^{-/-}$ mouse.

In some embodiments, the ocular and/or retinal disorders associated with aberrant all-trans-retinaldehyde and/or formation of retinaldehyde metabolites in the retina, which can be treated using the compounds described herein, can include, for example, retinal degeneration, macular degeneration, including age-related macular degeneration including the dry form and the wet form of age related macular degeneration, Stargardt disease, Stargardt macular degeneration, fundus flavimaculatus, geographic atrophy, retinitis pigmentosa, ABCA4 mutation related retinal dystrophies, vitelliform (or Best) macular degeneration, adult onset form of vitelliform macular dystrophy, Sorsby's fundus dystrophy, Malattia leventinese (Doyne honeycomb or dominant radial drusen), diabetic retinopathy, diabetic maculopathy, diabetic macular edema, retinopathy that is or presents geographic atrophy and/or photoreceptor degeneration, retinopathy that is a lipofuscin-based retinal degeneration, aberrant modulation of lecithin-retinol acyltransferase in an eye, Leber's congenital amaurosis, retinal detachment, hemorrhagic retinopathy, hypertensive retinopathy, hereditary or non-hereditary optic neuropathy, inflammatory retinal disease, retinal blood vessel occlusion, retinopathy of prematurity, ischemia reperfusion related retinal injury, proliferative vitreoretinopathy, retinal dystrophy, uveitis, retinal disorders associated with Alzheimer's disease, retinal disorders associated with multiple sclerosis, retinal disorders associated with Parkinson's disease, retinal disorders associated with viral infection (cytomegalovirus or herpes simplex virus), retinal disorders related to light overexposure or myopia, retinal disorders associated with AIDS, genetic retinal dystrophies, traumatic injuries to the optic nerve, such as by physical injury, excessive light exposure, or laser light, neuropathies due to a toxic agent or caused by adverse drug reactions or vitamin deficiency, progressive retinal atrophy or degeneration, retinal diseases or disorders resulting from mechanical injury, chemical or drug-induced injury, thermal injury, radiation injury, light injury, or laser injury, hereditary and non-hereditary retinal dystrophy, ophthalmic injuries from environmental factors, such as light-induced oxidative retinal damage, laser-induced retinal damage, "flash bomb injury," or "light dazzle", refractive errors including but not limited to myopia, and retinal diseases related to A2E accumulation including RDS/PHRP2-related macular degeneration, Batten disease (juvenile neuronal ceroid lipofuscinosis), and central serous chorioretinopathy.

In other embodiments, the ocular disorder treated by the compound can include at least one of light induced retinal degeneration, macular degeneration, Stargardt's disease, geographic atrophy, retinitis pigmentosa, Leber's congenital amaurorsis, and cone-rod dystrophy.

In some embodiments, the compounds described herein do not inhibit or do not substantially inhibit RPE65 and/or LRAT enzymatic activity or any other proteins involved in retinoid metabolism in the eye of the subject. Inhibition of retinoid isomerase (RPE65) can produce the highly undesirable side effect of severely delayed dark adaptation. Therefore, in certain embodiments, the retinal sequestering compounds for use in a method described herein do not inhibit RPE65 and subsequently do not cause delayed dark adaptation (i.e., night blindness) in a subject.

In other, the compounds described herein, which can inhibit retinal degeneration upon administration to a subject, can be selected using an in vitro assays that measure the ability of a CRBP antagonists to affect retinoid flux in the ocular tissue and in vivo assays that measure, chromophore regeneration and ERG and the optical coherence tomography score of retinas of Balb/cJ mice or Rdh8$^{-/-}$Abca4$^{-/-}$ mice exposed to intense light-induced retinal degeneration. In certain embodiments, the compounds described herein that can inhibit retinal degeneration upon administration to a subject do not significantly inhibit RPE65 activity in a subject's ocular tissue. In some embodiments, the compounds described herein when administered to a Rdh8$^{-/-}$ Abca4$^{-/-}$ mouse increase the optical coherence tomography score of the mouse in comparison to untreated control animal.

In other embodiments, a therapeutically effective amount of the CRBP antagonists or compounds described herein can be administered to a subject to treat an inflammatory and/or immune disorder associated with or affected by retinoic acid production in a subject in need thereof.

In some embodiments, the inflammatory and/or immune disorder associated with or affected by retinoic acid production in a subject, which can be treated by the compounds, can include at least one of achlorhydra autoimmune active chronic hepatitis, acute disseminated encephalomyelitis, acute hemorrhagic leukoencephalitis, Addison's disease, agammaglobulinemia, alopecia areata, Alzheimer's disease, amyotrophic lateral sclerosis, ankylosing spondylitis, anti-gbm/tbm nephritis, antiphospholipid syndrome, antisynthetase syndrome, aplastic anemia, arthritis, atopic allergy, atopic dermatitis, autoimmune cardiomyopathy, autoimmune hemolytic anemia, autoimmune hepatitis, autoimmune inner ear disease, autoimmune lymphoproliferative syndrome, autoimmune peripheral neuropathy, autoimmune polyendocrine syndrome, autoimmune progesterone dermatitis, autoimmune thrombocytopenia purpura, autoimmune uveitis, balo disease/balo concentric sclerosis, Bechets syndrome, Berger's disease, Bickerstaff's encephalitis, Blau syndrome, bullous pemphigoid, Castleman's disease, Chagas disease, chronic fatigue immune dysfunction syndrome, chronic inflammatory demyelinating polyneuropathy, chronic lyme disease, chronic obstructive pulmonary disease, Churg-Strauss syndrome, cicatricial pemphigoid, coeliac disease, Cogan syndrome, cold agglutinin disease, cranial arteritis, crest syndrome, Crohns disease, Cushing's syndrome, Dego's disease, Dercum's disease, dermatitis herpetiformis, dermatomyositis, diabetes mellitus type 1, Dressler's syndrome, discoid lupus erythematosus, eczema, endometriosis, enthesitis-related arthritis, eosinophilic fasciitis, epidermolysis bullosa acquisita, essential mixed cryoglobulinemia, Evan's syndrome, fibrodysplasia ossificans progressive, fibromyalgia, fibromyositis, fibrosing aveolitis, gastritis, gastrointestinal pemphigoid, giant cell arteritis, glomerulonephritis, Goodpasture's syndrome, Graves' disease, Guillain-barré syndrome (GBS), Hashimoto's encephalitis, Hashimoto's thyroiditis, henoch-schonlein purpura, hidradenitis suppurativa, Hughes syndrome, inflammatory bowel disease (IBD), idiopathic inflammatory demyelinating diseases, idiopathic pulmonary fibrosis, idiopathic thrombocytopenic purpura, iga nephropathy, inflammatory demyelinating polyneuopathy, interstitial cystitis, irritable bowel syndrome (IBS), Kawasaki's disease, lichen planus, Lou Gehrig's disease, lupoid hepatitis, lupus erythematosus, ménière's disease, microscopic polyangiitis, mixed connective tissue disease, morphea, multiple myeloma, multiple sclerosis, myasthenia gravis, myositis, narcolepsy, neuromyelitis optica, neuromyotonia, occular cicatricial pemphigoid, opsoclonus myoclonus syndrome, ord thyroiditis, Parkinson's disease, pars planitis, pemphigus, pemphigus vulgaris, pernicious anaemia, polymyalgia rheumatic, polymyositis, primary biliary cirrhosis, primary sclerosing cholangitis, progressive inflammatory neuropathy, psoriasis, psoriatic arthritis, raynaud phenomenon, relapsing polychondritis, Reiter's syndrome, rheumatoid arthritis, rheumatoid fever, sarcoidosis, schizophrenia, Schmidt syndrome, Schnitzler syndrome, scleritis, scleroderma, Sjøgren's syndrome, spondyloarthropathy, sticky blood syndrome, still's disease, stiff person syndrome, sydenham chorea, sweet syndrome, takayasu's arteritis, temporal arteritis, transverse myelitis, ulcerative colitis, undifferentiated connective tissue disease, undifferentiated spondyloarthropathy, vasculitis, vitiligo, Wegener's granulomatosis, Wilson's syndrome, Wiskott-Aldrich syndrome, hypersensitivity reactions of the skin, atherosclerosis, ischemia-reperfusion injury, myocardial infarction, and restenosis, fulminating or disseminated pulmonary tuberculosis when used concurrently with appropriate chemotherapy, hypersensitivity pneumonitis, idiopathic bronchiolitis obliterans with organizing pneumonia, idiopathic eosinophilic pneumonias, idiopathic pulmonary fibrosis, *Pneumocystis carinii* pneumonia (PCP) associated with hypoxemia occurring in an HIV(+) individual who is also under treatment with appropriate anti-PCP antibiotics, a diuresis or remission of proteinuria in nephrotic syndrome, without uremia, of the idiopathic type or that due to lupus erythematosus, ankylosing spondylitis, polymyalgia rheumatic, psoriatic arthritis, relapsing polychondritis, trichinosis with neurologic or myocardial involvement, and tuberculous meningitis.

In other embodiments, inflammatory the disorder can include inflammation of the esophagus, inflammation of the glottis, inflammation of the epiglottis, inflammation of the tonsils, inflammation of the oropharynx, eosinophilic esophagitis, gastroesophageal reflux disease (GERD), non-erosive reflux disease (NERD), erosive esophagitis, Barrett's esophagus, eosinophilic gastroenteritis, hypereosinophilic syndrome, corrosive (caustic) chemical esophagitis, radiation-induced esophagitis, chemotherapy-induced esophagitis, transient drug-induced esophagitis, persistent drug-induced esophagitis, Crohn's disease of the esophagus, and pseudomembranous esophagitis.

In still other embodiments, the inflammatory and/or immune disorder can include at least one of oral ulcers, gum disease, gastritis, colitis, ulcerative colitis, gastric ulcers, inflammatory bowel disease, and Crohn's disease.

In other embodiments, the metabolic disorders associated with dysregulation of lipid homeostasis in a subject, which can be treated by the compounds, can include at least one of obesity, obesity-related conditions, dyslipidemia, non-alcoholic fatty liver disease, liver steatosis, and metabolic syndrome.

The compounds described herein used in methods described herein can be administered to the subject to treat the ocular disorder (e.g., macular degeneration or Stargardt disease), inflammatory disorder, and/or immune disorder, and metabolic disorders using standard delivery methods including, for example, ophthalmic, topical, parenteral, subcutaneous, intravenous, intraarticular, intrathecal, intramuscular, intraperitoneal, intradermal injections, or by transdermal, buccal, oromucosal, oral routes or via inhalation. The particular approach and dosage used for a particular subject depends on several factors including, for example, the general health, weight, and age of the subject. Based on factors such as these, a medical practitioner can select an appropriate approach to treatment.

Generally, the effective amount of the compound may be in the range of about 1 to 1,000 mg in the oral administration, about 0.1 to 500 mg in the intravenous administration, about 5 to 1,000 mg in the topical administration or 1 to 500 mg by inhalation. Generally, the daily dosage for adults is in the range of about 0.1 to 5,000 mg, preferably about to 1,000 mg, but cannot be determined uniformly because it depends on age, sex, body weight and the physical condition of the patients to be treated. The formulation may be administered once a day or several times a day with a divided dose.

Treatment according to the method described herein can be altered, stopped, or re-initiated in a subject depending on the status of ocular disorder. Treatment can be carried out as intervals determined to be appropriate by those skilled in the art. For example, the administration can be carried out 1, 2, 3, or 4 times a day. In another embodiment, the compounds described herein can be administered after induction of macular degeneration has occurred.

The treatment methods can include administering to the subject a therapeutically effective amount of the compounds described herein. Determination of a therapeutically effective amount is within the capability of those skilled in the art. The exact formulation, route of administration, and dosage can be chosen by the individual physician in view of the subject's condition.

Formulation of pharmaceutical compounds for use in the modes of administration noted above (and others) are described, for example, in Remington's Pharmaceutical Sciences (18th edition), ed. A. Gennaro, 1990, Mack Publishing Company, Easton, Pa. (also see, e.g., M. J. Rathbone, ed., Oral Mucosal Drug Delivery, Drugs and the Pharmaceutical Sciences Series, Marcel Dekker, Inc., N.Y., U.S.A., 1996; M. J. Rathbone et al., eds., Modified-Release Drug Delivery Technology, Drugs and the Pharmaceutical Sciences Series, Marcel Dekker, Inc., N.Y., U.S.A., 2003; Ghosh et al., eds., Drug Delivery to the Oral Cavity, Drugs and the Pharmaceutical Sciences Series, Marcel Dekker, Inc., N.Y. U.S.A., 1999.

In one example, the compounds or CRBP antagonists described herein can be provided in an ophthalmic preparation that can be administered to the subject's eye. The ophthalmic preparation can contain the compounds described herein in a pharmaceutically acceptable solution, suspension or ointment. Some variations in concentration will necessarily occur, depending on the particular retinal sequestering compound employed, the condition of the subject to be treated and the like, and the person responsible for treatment will determine the most suitable concentration for the individual subject. The ophthalmic preparation can be in the form of a sterile aqueous solution containing, if desired, additional ingredients, for example, preservatives, buffers, tonicity agents, antioxidants, stabilizers, nonionic wetting or clarifying agents, and viscosity increasing agents.

Examples of preservatives for use in such a solution include benzalkonium chloride, benzethonium chloride, chlorobutanol, thimerosal and the like. Examples of buffers include boric acid, sodium and potassium bicarbonate, sodium and potassium borates, sodium and potassium carbonate, sodium acetate, and sodium biphosphate, in amounts sufficient to maintain the pH at between about pH 6 and about pH 8, and for example, between about pH 7 and about pH 7.5. Examples of tonicity agents are dextran 40, dextran 70, dextrose, glycerin, potassium chloride, propylene glycol, and sodium chloride.

Examples of antioxidants and stabilizers include sodium bisulfite, sodium metabisulfite, sodium thiosulfite, and thiourea. Examples of wetting and clarifying agents include polysorbate 80, polysorbate 20, poloxamer 282 and tyloxapol. Examples of viscosity-increasing agents include gelatin, glycerin, hydroxyethylcellulose, hydroxmethylpropylcellulose, lanolin, methylcellulose, petrolatum, polyethylene glycol, polyvinyl alcohol, polyvinylpyrrolidone, and carboxymethylcellulose. The ophthalmic preparation will be administered topically to the eye of the subject in need of treatment by conventional methods, for example, in the form of drops or by bathing the eye in the ophthalmic solution.

The compounds described herein can also be formulated for topical administration through the skin. "Topical delivery systems" also include transdermal patches containing the ingredient to be administered. Delivery through the skin can further be achieved by iontophoresis or electrotransport, if desired.

Formulations for topical administration to the skin can include, for example, ointments, creams, gels and pastes comprising the compounds in a pharmaceutical acceptable carrier. The formulation of the compounds for topical use includes the preparation of oleaginous or water-soluble ointment bases, as is well known to those in the art. For example, these formulations may include vegetable oils, animal fats, and, for example, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin and glyceryl monostearate. Various water-soluble ointment bases may also be used, including glycol ethers and derivatives, polyethylene glycols, polyoxyl 40 stearate and polysorbates.

In some embodiments, subjects affected with or at risk of macular degeneration, which are not readily accessible or suitable for ophthalmic (e.g. eye-drops) and/or topical administration and/or that have inflammatory and/or immune disorders, can be treated by a systemic approach, such as oral, enteral, or intravenous infusion. For example, compounds described herein can be administered at a low dosage by continuous intravenous infusion.

In another example, in which a patient requires longer-term care, the CRBP antagonists described herein can be administered intermittently (e.g., every 12-24 hours). In a variation of this approach, the initial or loading dose can be followed by maintenance doses that are less than, (e.g., half) the loading dose or by continuous infusion. The duration of such treatment can be determined by those having skill in the art, based on factors, for example, the severity of the condition and the observation of improvements.

When administering the compounds described herein to the subject by intravenous infusion, devices and equipment (e.g., catheters, such as central or peripheral venous catheters, tubing, drip chambers, flashback bulbs, injection Y sites, stopcocks, and infusion bags) can be used that are compatible with the retinal sequestering compound.

As discussed above, the compounds described herein may be administered to a subject in order to treat or prevent macular degeneration and other forms of retinal disease whose etiology involves elevated levels of toxic all-trans-retinaldehyde in a subject. Other diseases, disorders, or conditions characterized by increased or excessive all-trans-retinaldehyde in ocular tissue may be similarly treated.

In one embodiment, a subject is diagnosed as having symptoms of macular degeneration, and then a disclosed compound is administered. In another embodiment, a subject may be identified as being at risk for developing macular degeneration (risk factors include a history of smoking, age, female gender, and family history), and then a disclosed compound is administered. In another embodiment, a subject may have dry AMD in both eye, and then a disclosed compound is administered. In another embodiment, a subject may have wet AMD in one eye but dry AMD in the other eye, and then a disclosed compound is administered. In yet another embodiment, a subject may be diagnosed as having Stargardt disease and then a disclosed compound is administered. In another embodiment, a subject is diagnosed as having symptoms of other forms of retinal disease whose etiology involves increased all-trans-retinaldehyde in ocular tissue of a subject, and then the compound is administered. In another embodiment, a subject may be identified as being at risk for developing other forms of retinal disease whose etiology involves increased all-trans-retinaldehyde in ocular tissue, and then the disclosed compound is administered. In some embodiments, a compound is administered prophylactically. In some embodiments, a subject has been diagnosed as having the disease before retinal damage is apparent. In some embodiments, a human subject may know that he or she is in need of the macular generation treatment or prevention.

In some embodiments, a subject may be monitored for the extent of macular degeneration. A subject may be monitored in a variety of ways, such as by eye examination, dilated eye examination, fundoscopic examination, visual acuity test, and/or biopsy. Monitoring can be performed at a variety of times. For example, a subject may be monitored after a compound is administered. The monitoring can occur, for example, one day, one week, two weeks, one month, two months, six months, one year, two years, five years, or any other time period after the first administration of a compound. A subject can be repeatedly monitored. In some embodiments, the dose of a compound may be altered in response to monitoring.

In some embodiments, the disclosed methods may be combined with other methods for treating or preventing macular degeneration or other forms of retinal disease whose etiology involves increased all-trans-retinaldehyde in ocular tissue, such as photodynamic therapy. For example, a patient may be treated with more than one therapy for one or more diseases or disorders. For example, a patient may have one eye afflicted with dry form AMD, which is treated with a compound of the invention, and the other eye afflicted with wet form AMD, which is treated with, e.g., photodynamic therapy.

The invention is further illustrated by the following example, which is not intended to limit the scope of the claims.

Example

In our attempt to influence vitamin A metabolism for therapeutic benefit via pharmacologic methods, we hypothesized that targeting retinol carriers inside cells might represent a safer and more specific alternative than RBP4 inhibitors. There are four representatives of the CRBP protein family in the human genome (CRBP1-4). Although they are structurally similar, their affinities for atROL range between less than 1 nM for CRBP1 to 200 nM for CRBP4. CRBPs also differ in their relative abundance and tissue distribution, which may suggest diverse and cell-specific functions for these proteins. The most ubiquitous is CRBP1 (encoded by the RBP1 gene). Although present in numerous tissues, it is particularly abundant in hepatocytes and the retinal pigment epithelium (RPE), where it enhances intracellular vitamin A uptake. The role of CRBP1 in RPE cells is principally important. CRBP1 is directly involved in the regeneration of visual chromophore via the retinoid cycle by facilitating both the recycling of vitamin A from photoreceptor cells and its efficient esterification. Studies on CRBP1-deficient mice ($Rbp1^{-/-}$) revealed a diminished amount of all-trans-retinyl esters in the RPE and the transient accumulation of atROL upon recovery from exposure to bright light. This physiological function of CRBP1 preordains this protein to become a potential pharmaceutical target for modulating the flux of retinoids via the visual cycle and, thus, offers an opportunity to manage the pathological processes associated with an imbalance in ocular retinoid homeostasis. Importantly, the deactivation of the Rbp1 gene does not cause spontaneous pathological changes in the murine retina.

To test this hypothesis, we developed a high-throughput screening (HTS) methodology that led to the identification of abnormal cannabidiol (abn-CBD) as a potent nonretinoid ligand of CRBP1. We delineated the mode of protein-ligand interaction at the atomic level by solving high-resolution X-ray structures of CRBP1 in complex with abn-CBD and its derivatives. We also examined the effects of abn-CBD on ocular vitamin A homeostasis in vivo and provided evidence that the systemic administration of this compound protects mouse retinas from light-induced damage. Thus, we discovered a first-in-class drug candidate that affects retinoid metabolism by targeting CRBPs.

Materials and Methods

Chemicals and Reagents

4-[(1R,6R)-3-Methyl-6-prop-1-en-2-ylcyclohex-2-en-1-yl]-5-pentylbenzene-1,3-diol (abn-CBD) was purchased form Cayman Chemical Company and Toronto Research Chemicals. Derivatives of abn-CBD including 4-[(6R)-3-methyl-6-(1-methylethenyl)-2-cyclohexen-1-yl]-5-pentyl-1,3-benzenediol-5,5,5-d3 (3d-abn-CBD), 5-methyl-4-[(1R,6R)-3-methyl-6-prop-1-en-2-ylcyclohex-2-en-1-yl]benzene-1,3-diol (abn-CBDO), 5-methyl-2-[(6R)-3-methyl-6-prop-1-en-2-ylcyclohex-2-en-1-yl]benzene-1,3-diol (CBDO), and 1,3-dimethoxy-5-methyl-2-[(1R,6R)-3-methyl-6-prop-1-en-2-ylcyclohex-2-en-1-yl]benzene (O-1918) were obtained from Cayman Chemical Company. The racemic mixture of limonene was obtained from Sigma-Aldrich. atROL was purchased from Toronto Research Chemicals, whereas 11-cis-retinol was produced as described in Arne et al. HPLC-grade organic solvents used in this study were purchased from Thermo Fisher Scientific.

Animals and Animal Care

Balb/cJ mice at five to eight weeks of age were purchased from The Jackson Laboratory. All mice were housed in the Animal Resource Center at the School of Medicine, Case Western Reserve University (CWRU), and fed with a standard laboratory mouse diet supplemented with 10-12 IU g-1 of vitamin A. Mice were dark adapted for at least 24 h prior to experiments. Manipulations in the dark were performed under dim red light. All animal procedures and experimental protocols were approved by the Institutional Animal Care and Use Committee at CWRU and confirmed to recommendations of both the American Veterinary Medical Association Panel on Euthanasia as well as the Association for Research in Vision and Ophthalmology.

Expression and Purification of CRBP1

Human apo-CRBP1 was expressed and purified as described by Silvaroli et al. (J Biol Chem. 2016, 15; 291 (16)) without any further modification to the established protocol.

Expression and Purification of CRBP2

The cDNA of human CRBP2 was purchased from Origene Technologies and amplified by polymerase chain reaction (PCR) to subclone into pET30b expression vector (Millipore Sigma), thereby modifying the C-terminal sequence to introduce thrombin cut site that allowed for removal of a 6× histidine tag from the purified protein. The recombinant protein was expressed in the BL21 (DE3) *E. coli* strain (New England Biolabs). The bacteria were grown at 37° C. in the presence of 50 μM kanamycin to OD600=0.6-0.8 prior to addition of isopropyl β-D-1 thiogalactopyranoside (Roche) to a final concentration of 0.5 mM. After 4 h of incubation, the cells were harvested by centrifugation (6,000 g, 15 min, 4° C.). Bacteria were disrupted by osmotic shock, and the lysate was centrifuged at 36 000 g for 30 min at 4° C. The supernatant was collected, and its buffer composition was adjusted to match the loading buffer (50 mM Tris-HCl, pH 8.0, 250 mM NaCl). Next, the protein was loaded onto a 5 mL HisTrap column (GE Healthcare). The column was washed with 100 mL of the loading buffer containing 5 mM imidazole prior to the elution of bound proteins with 250 mM imidazole. Eluted fractions were examined by sodium dodecyl sulfate polyacrylamide gel electrophoresis (SDS-PAGE), combined, and concentrated to 5 mL in an Amicon Ultra-4 centrifugal filter, cutoff 10 000 Da (Millipore). The protein was loaded onto a gel filtration column Superdex 200 (GE Healthcare) equilibrated with 10 mM Tris/HCl buffer, pH 8.0. Fractions containing CRBP2 were pooled together and incubated with thrombin (USB Affymetrix) for 16 h at 4° C. to remove the histidine tag. After the ion strength of the protein solution was adjusted by adding NaCl to the final concentration of 300 mM, digested CRBP2 was reloaded onto a HisTrap column. Unbound fraction that contained digested protein was collected, diluted 20 times with 10 mM Tris/HCl buffer, pH 8.0 buffer, and loaded onto HiTrap Q HP ion exchanger column (GE Healthcare) for the final step of purification. CRBP2 was eluted with a gradient of NaCl (0-0.5 M) over 30 min at a flow rate 1.0 mL $min^{-1}$. Purity of the collected protein fractions were checked by SDS-PAGE. The mass of an intact protein was verified by mass spectrometry. Purified CRBP2 was concentrated to ~9 mg $mL^{-1}$, and 0.2 mL aliquots were stored at −80° C.

Expression and Purification of CRBP3

The cDNA of human CRBP3 was purchased from Origene Technologies. To introduce a thrombin cut site at the C-terminus of the protein, the cDNA was amplified by PCR and subcloned into pET30b vector. The next steps of the expression and purification of CRBP3 were identical to the procedure described above for CRBP2.

Expression and Purification of CRBP4

The cDNA of human CRBP4 was purchased from Origene Technologies. The introduction of a thrombin cut site at the C-terminus was achieved by PCR amplification of the cDNA. The PCR product was subcloned into pET30b vector. For the most part, CRBP4 was expressed and purified as described for CRBP2. However, after digestion with thrombin and reloading onto HisTrap column, the unbound fraction of the protein was further purified on a HiTrap SP HP ion exchanger column (GE Healthcare). CRBP4 was loaded in 10 mM Tris/HCl buffer, pH 8.0 buffer, and subsequently eluted with a gradient of NaCl (0-0.5 M) over 30 min at a flow rate 1.0 mL $min^{-1}$. Purified CRBP4 was concentrated to 6 mg $mL^{-1}$ and liquated at −80° C.

Obtaining CRBP1 in Complex with atROL

To prepare holo-CRBP1, 3 mg of purified apoprotein was incubated for 15 min on ice with 2 molar excess of atROL (Toronto Research Chemicals) in 10 mM Tris-HCl, pH 8.0, 5% glycerol (v/v). The retinoid was delivered in acetonitrile (<1%, v/v). To remove excess of atROL, the protein solution was diluted 10× with 10 mM Tris-HCl, pH 8.0, centrifuged (36 000 g, 20 min, 4° C.) and loaded onto a 5 mL HiTrap Q HP column. Holo-CRBP1 was eluted from the column in conditions described in CRBP1 purification method. The efficiency of formation of holo-CRBP1 was examined by recording UV/vis spectrum of the repurified protein. The complex of CRBP1 with atROL revealed characteristic absorbance spectrum with maxima at 282 nm, corresponding to the protein scaffold and triple maxima at 332, 348, and 365 nm, indicating bound retinoid.

Fluorescence Binding Assays

Figure 2A:
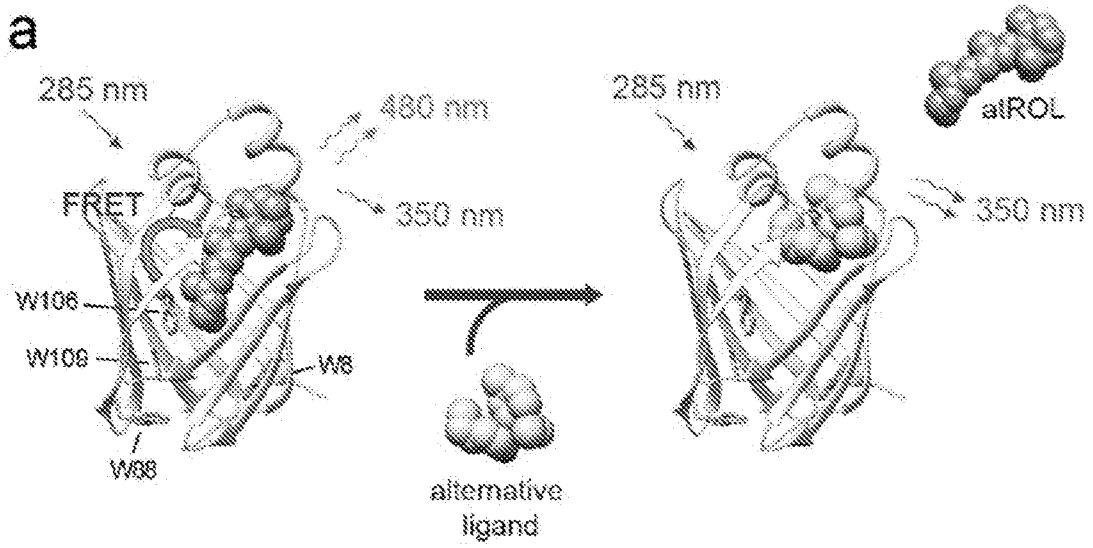
FIGS. 2(A-C) illustrate schematics and plots showing biophysical principles and the results of the high-throughput screening (HTS) for CRBP1 ligands. (A) A schematic representation of the vitamin A-displacement assay. Replacement or liberation of atROL from holo-CRBP1 by an alternative nonretinoid ligand results in diminishing of FRET between the retinoid moiety and the protein scaffold. (B) Differences in the fluorescence emission spectra between CRBP1 in complex with atROL and the apo form of the protein were used as a readout in a high-throughput assay. (C) The primary screening of a chemical library composed of bioactive lipids revealed a single hit that corresponded to a synthetic derivative of cannabidiol, abn-CBD.
Figure 2B:
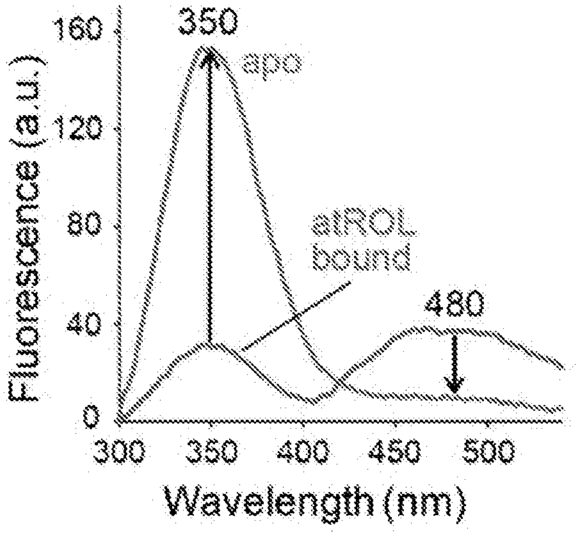

The apparent affinity of nonretinoid ligands was evaluated by monitoring changes in the fluorescence of holo-CRBP1. In the atROL bound form, the protein excited at 285 nm emitted fluorescence at 350 and 480 nm due to FRET between the protein scaffold and the retinoid moiety (FIG. 2A). Replacement of atROL in the binding site by tested ligands leads to disruption of FRET and consequently an increase in the fluorescence intensity at 350 nm with concomitant diminishing signal at 480 nm. All fluorescence measurements were performed using a PerkinElmer Life Sciences LS55 spectrofluorometer. The titrations were performed at 25° C. in 67 mM phosphate-buffered saline buffer, pH 7.4, containing 5% glycerol (v/v) by adding an increasing amount of an examined compound delivered in acetonitrile. The final concentrations of the organic solvent did not exceed 0.4% of the sample's total volume. All fluorescence spectra were corrected for the inner filter effect. The Ki values were calculated by fitting intensities of the protein fluorescence at the maximum emission (350 nm) or the intensity of retinoid fluorescence at 480 nm to the saturation single ligand-binding model. The data fitting and calculations of the Ki values were performed using SigmaPlot 11 software package (Systat Software).

High-Throughput Screening for CRBP1 Ligands

The principle of the fluorescence binding assays described above was adapted for the HTS in a 96-well plate format. Each well contained 0.2 mL of 20 mM Tris/HCl, pH 7.4 and 1 μM of holo-CRBP1. Tested compounds from two independent libraries (Bioactive Lipid I Screening Library form Cayman Chemicals and Screen-Well Bioactive Lipid Library from Enzo Life Science, total of 986 chemicals) were delivered in dimethyl sulfoxide (DMSO) to the final concentration of 5 μM. After 15 min of incubation at room temperature (RT), the samples were excited at 285 nm, and the fluorescence signals from CRBP1 (at 350 nm) and atROL (at 480 nm) were recorded in a Flexstation3 microplate reader (Molecular Devices). Changes in the fluorescence emissions were evaluated by calculating ratio between signals at 480 and 350 nm. To eliminate false positives, only those wells in which the increase in protein fluorescence was accompanied by proportional decline in the fluorescence of atROL were considered as potential hits.

Retinol Replacement Assay holo-CRBP1 (500 μg) in 0.5 mL (67 μM) was incubated with tested compound (1:2 molar ratio) delivered in ethanol in 20 mM Tris/HCl, pH 8.0, 200 mM NaCl, 5% glycerol (v/v) at RT for 15 min. The sample was then diluted with 10 mM Tris/HCl, pH 8.0 to the final volume of 5 mL, loaded onto HiTrap Q HP column, and eluted as described above. The elution profiles were monitored at both 280 and 325 nm to concurrently record signals for the protein and the retinoid moieties.

Mass Spectrometry Analysis

After incubation of apo- or holo-CRBP1 with abn-CBD, the protein was repurified on HiTrap Q HP column as described above. The protein fractions were collected, pooled together, and concentrated to 0.25 mL in an Amicon Ultra-4 centrifugal filter, cutoff 10,000 Da. For quantification purpose, 100 pmol of 3d-abn-CBD (internal standard) were added to the protein samples. To extract organic compounds associated with the repurified CRBP1, 0.25 mL of ethanol was added followed by 4 mL of hexane. The sample were shaken vigorously and centrifuged at 26,000 g for 5 min. The resulting supernatant was dried under a stream of nitrogen, and the residual compounds were resuspended in 0.3 mL of ethanol. The samples were injected onto an X-Bridge C18 column, 3.5 μm, 2.1×100 mm (Waters) equilibrated with 30% water in methanol (v/v). Abn-CBD was eluted in a gradient of methanol in water (70% to 100%) developed over 10 min at a flow rate 0.5 mL $min^{-1}$. The eluent was directed into an LTQ ion trap mass spectrometer (Thermo Scientific) via an electrospray ionization source working in the positive mode. The mass spectrometer operation parameters were optimized using synthetic abn-CBD standard. Abn-CBD and its deuterated derivative were detected in the selected reaction monitoring (SRM) mode using m/z 315.2→221.2 and 318.2→224.1 transitions, respectively. Calibration curves were calculated based on the linear relationship between areas under SRM ion intensity for peaks corresponding to abn-CBD and the internal standard versus molar ratios of these compounds in a range from 20 to 500 pmol.

Detection and Quantification of abn-CBD in the Ocular Tissues

Balb/cJ mice were i.p. injected with 15 mg kg-1 dose of abn-CBD. At the time points between 1 and 15 h, they were deeply anesthetized by ketamine/xylazine injection and perfused with PBS. Perfused eyes were collected and homogenized in 1 mL of PBS/methanol (v/v). During the homogenization, 100 pmol of an internal standard (3d-abn-CBD) was added. The samples were extracted with 4 mL of hexane and centrifuged at 15,000 g for 5 min at 4° C. The organic solvent was transferred to glass test tubes and dried in a Savant speedvac concentrator (Thermo Fisher Scientific). The extracted compounds were dissolved in 0.3 mL of ethanol and subjected to LC/MS analysis and quantification as described above.

Crystallization of CRBPs

Crystals of CRBP1 in complex abn-CBD and its derivatives (abn-CBDO or CBDO) were grown essentially as described by Silvaroli et al (ACS Chem Biol. 2019, 15; 14(3)). The apo protein at 3 mg mL-1 was preincubated with 300 μM of a ligand in 10 mM Tris-HCl buffer, pH 8.0, 150 mM NaCl for 15 min on ice. This sample (1 μL) was mixed in 1:1 ratio with a crystallization solution composed of 0.1 M BisTris, pH 5.5, and 25% poly(ethylene glycol) (PEG) 3350 (w/v). Crystals of CRBP3 with abn-CBD were obtained by preincubating apoprotein at 8 mg mL-1 with 300 μM of the ligand for 15 min and setting up crystallization drops by mixing 1 μL of the protein sample with 1 μL of 0.2 M sodium malonate, pH 5.0 and 20% PEG 3350 (w/v) solution. For CRBP4, the crystallization conditions included 0.2 M NaCl, 0.1 M BisTris, pH 6.5, and 25% PEG 3350 (w/v). Similar to the other CRBPs, CRBP4 (6 mg $mL^{-1}$) was preincubated with abn-CBD prior to the crystallization. All of the protein crystals were obtained by the sitting drop vapor diffusion method at RT. Mature crystals were collected and flash-cooled in liquid nitrogen in preparation for X-ray diffraction experiments.

X-Ray Data Collection, Processing, and Model Building

X-ray diffraction data were collected at the Advanced Photon Source beamlines NE-CAT 24-ID-C and 24-ID-E or Stanford Synchrotron Radiation Lightsource beamline 9-2. Data from single crystals were integrated and scaled with MOSFLM. The structures of CRBPs in complexes with its ligands were solved by molecular replacement with PHASER_MR using the following structural templates: PDB No. 5HBS, 1GGL, and 1LPJ for CRBP1, 3, and 4, respectively. Initial models were manually adjusted in COOT and refined with PHENIX using a riding hydrogen model, individual anisotropic temperature factors, and occupancy refinement for alternative conformers and waters. Geometry of the refined model was verified with the MolProbity server. The accession codes as well as the data collection and refinement statistics. Visualization of the macromolecules were performed in the CHIMERA software package version 1.12.

Photobleaching and Visual Chromophore Regeneration Protocols

Balb/cJ mice were dark adapted for at least 24 h before the experiment. Mouse pupils were dilated with 1% tropicamide, and the animals were subjected to a single light flash from a photographic flash unit TT560 (Neewer) at the maximum setting that resulted in photobleach of ~-70% of visual pigment. After the light exposure, the mice were kept in dark and euthanized at time intervals between 1 min to 8 h. The eyes were removed, flash frozen in liquid nitrogen, and stored in −80° C. until retinoid analysis.

Detection and Quantification of Ocular Retinoids

All procedures related to the retinoid analysis were done under dim red light. To extract retinoids, enucleated eyes were transferred to a glass/glass homogenizer and submerged in 1 mL of 40 mM hydroxylamine in a 1:1 solution of PBS/methanol (v/v). The eyes were thoroughly homogenized and incubated at RT for 20 min to allow derivatization of retinylaldehydes to retinaldehdye oximes. The retinoids were extracted with 4 mL of hexane. To facilitate the fraction separation, the samples were centrifuged at 5000 g for 10 min, after which the upper organic phase was collected in a glass test tube. The organic solvent was dried in a rotary SpeedVac, and the residual retinoids were redissolved in 250 mL of hexanes, and subjected to HPLC analysis. Separation of retinoids was achieved on a normal phase column (Agilent Zorbax Sil 5 μm 4.6×250 mm) in a step gradient of ethyl acetate in hexane (1% for 10 min followed by 10% for 40 min at a constant flow rate of 1.5 mL $min^{-1}$). Elution of retinoids was monitored at 325 and 360 nm wavelengths. All-trans-retinyl esters, all-trans- and 11-cis-retinaldehdye oximes as well as atROL were identified based on their elution times and characteristic UV/vis spectra. Retinoids were quantified based on linear correlations between the amount of injected synthetic standards and the area under chromatographic peaks.

Retinol Esterification Assay

The enzymatic activity of LRAT was assayed using isolated UV-treated bovine RPE microsomes as described previously. The reaction mixture included 20 mM Tris/HCl buffer, pH 7.4, 1 mM DTT, 1% bovine serum albumin (BSA; w/v), and RPE microsomes (~100 μg of total protein) in the total volume of 0.1 mL. To test the influence of abn-CBD on the LRAT activity, 10, 20, or 50 μM of this compound was added prior to the addition of atROL (final concentration of 10 μM). To record the initial rate of the esterification, the mixture was incubated at RT for 5 min. The reaction was quenched with 0.2 mL of methanol, and the retinoids were extracted with 0.3 mL of hexane. The extracted retinoids were separated on a normal phase column (Agilent Zorbax Sil 5 μm 4.6×250 mm) in an isocratic flow of 10% ethyl acetate in hexane (flow rate of 1.5 mL $min^{-1}$). Elution of retinoids was monitored at 325 nm. All-trans-retinyl esters were quantified based on a correlation between the amount of injected synthetic standards and the area under chromatographic peaks.

11-cis-Retinol Oxidation Assay

Dehydrogenase activity was assayed by monitoring oxidation of 11-cis-retinol to a corresponding aldehyde in bovine RPE microsomes. The reaction mixture containing 20 mM Tris/HCl buffer, pH 8.0, 1% BSA (w/v), 20 μM NAD+, and RPE microsomes (~100 μg of total protein) in the total volume of 0.1 mL. 11-cis-Retinol (10 μM) was incubated at 30° C. for 10 min. The reaction was stopped by 0.2 mL of methanol that contained 40 mM hydroxylamine. After subsequent 15 min of incubation at RT, the retinoids were extracted with 0.3 mL of hexane and analyzed by normal-phase HPLC as described for the retinol esterification assay.

RPE65 Isomerization Activity Assay

For the retinoid isomerization assay, UV-bleached RPE microsomes isolated from bovine eyes served as a source of robust RPE65 enzymatic activity. The isomerization reaction was performed in the presence of cellular retinaldehyde-binding protein (CRALBP) according to an established methodology published previously. The enzymatic reaction was initiated by addition of atROL the final concentration of 10 μM. After incubation at 30° C. for 30 min, the reaction products were extracted with hexane and analyzed by HPLC as described above.

Light-Induced Retinal Degeneration

Retinal degeneration was induced by exposing dark-adapted Balb/cJ mice to white light with an intensity of ~50 000 lx, delivered from a 100 W AC90-145 V lightemitting diode (LED) lamp (Home Depot) for 1 h. Abn-CBD in doses of 30, 15, or 7.5 mg $kg^{-1}$ was administered by i.p. injection in sterilized 80% DMSO/water (v/v) 1 h before exposure to bright light. The injection volume did not exceed 25 μL. Retinal morphology was analyzed in vivo by OCT 7 d after the light exposure. Then the mice were euthanized, and their eyes were subjected to staining with H&E staining and imaging.

Optical Coherence Tomography (OCT)

To assess the effect of abn-CBD on light-induced retinal degeneration in Balb/cJ mice, the retinas were examined by ultrahigh resolution OCT (Bioptigen). Pupils of mice were first dilated with 1% tropicamide, and the animals were anesthetized with ketamine/xylazine cocktail. Twenty-five frames of OCT images scanned at 0° and 900 were acquired in the B-scan and averaged.

Electroretinography (ERG) Analyses

Before the ERG recording, dark-adapted Balb/cJ mice were anesthetized with 20 mg $mL^{-1}$ ketamine and 1.75 mg $mL^{-1}$ xylazine in PBS at a dose of 0.1-0.13 mL per 25 g of body weight, and pupils were dilated with 1% tropicamide. Contact lens electrodes were placed on the eyes, and a reference electrode was positioned between two ears, while ground electrode was placed on the tail. Scotopic ERGs were recorded for both eyes of each mouse using a UTAS E-3000 universal testing and ERG system (LKC Technologies). To evaluate an effect of abn-CBD on retinal function, ERGs were performed on the control and abn-CBD-treated group of mice 4 h after exposure to a light illumination that resulted in photobleach 40% of visual pigment.

Retinal Histology

The structural morphology of mouse retinas challenged with bright light were assessed using H&E staining of paraffin sections. Mouse eyes were fixed in 4% paraformaldehyde and 1% glutaraldehyde followed by paraffin sectioning. Paraffin sections (5 μm thick) were stained with H&E and imaged by light microscopy (Leica).

Statistical Analysis

Four to six mice per treatment group were used. The data are expressed as mean±standard deviation (sd). For two-group comparisons, student's t test was performed, whereas for multiple groups comparisons, one-way ANOVA was used. Differences were considered statistically significant at p-value of less than 0.05.

Results

The Identification of abn-CBD as a Ligand for CRBP1

Figure 2C:
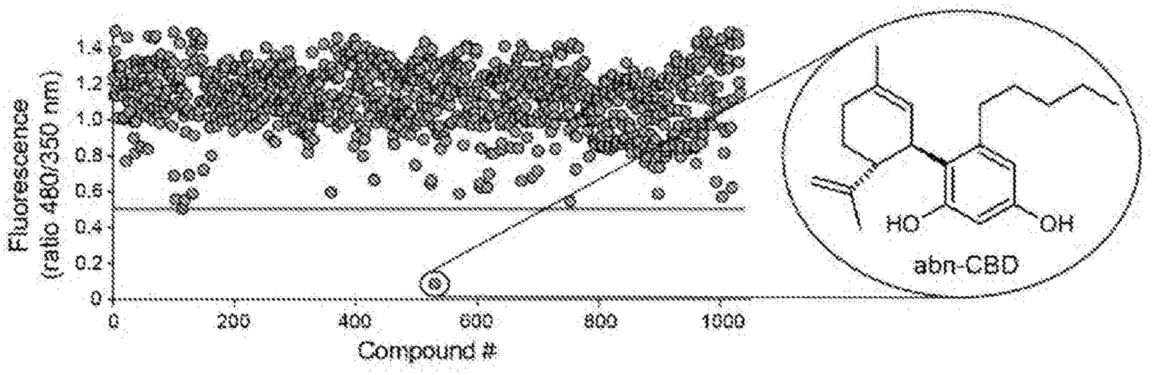

To search for compounds interacting with CRBP1, we developed an HTS strategy that minimalized experimental bias associated with investigating the binding of hydrophobic ligands to a protein specialized for interaction with small lipophilic molecules. It is based on the fluorescence properties of CRBP1 in complex with its natural ligand, atROL. The excitation of the protein scaffold by 285 nm light leads to a robust fluorescence resonance energy transfer (FRET) between the tryptophan residues and the retinoid moiety. Consequently, two maxima at 350 and 480 nm are observed in the CRBP1 fluorescence emission spectrum corresponding fluorescence emission from tryptophan residues and atROL, respectively. Upon the liberation of atROL or its replacement from the binding site by an alternative molecule, the efficiency of FRET decreases, leading to a dramatic increase in the fluorescence signal at 350 nm accompanied by a proportional drop in the emission at 480 nm (FIG. 2A,B). The signal intensities for apo-CRBP1 and CRBP1/atROL complex were used as the 0% and +100% change controls, respectively. The final assay quality was characterized by a Z'-factor of 0.61, a signal-to-background ratio of 14.3, and a coefficient of variation of 10.5%. The HTS was performed using 986 compounds from the Bioactive Lipid I Screening (Cayman Chemicals) and Screen-Well Bioactive Lipid (Enzo Life Science) libraries. After the elimination of duplicated molecules and compounds with spectral properties interfering with the fluorescence assay, the HTS revealed a unique hit that corresponded to abnormal cannabidiol (abn-CBD; FIG. 2C). This synthetic derivative of plant cannabidiol does not interact with cannabinoid receptor 1 or 2 and, thus, does not cause psychoactive effects.

Figure 3A:
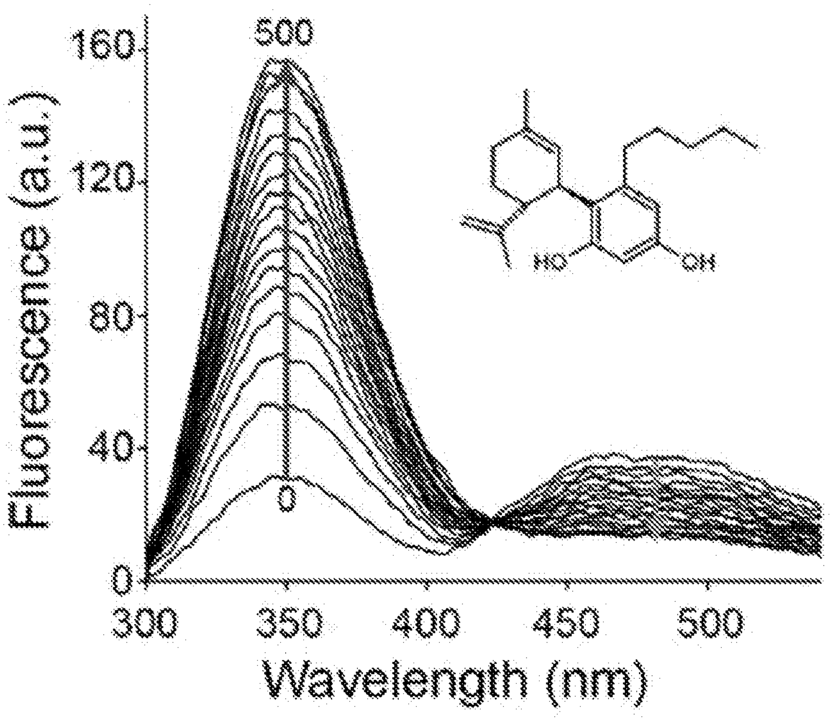
FIGS. 3(A-B) illustrate plots showing the determination of the Ki values for abn-CBD. (A) Fluorescence spectra of holo-CRBP1 upon titration with abn-CBD. (B) Changes in the emission maxima at 350 and 480 nm (inset) plotted vs concentration of abn-CBD were fitted to the one-site saturation ligand-binding model ($R_{sqr}$=0.997 and 0.990 for the fluorescence signal at 350 and 480 nm, respectively) and used to calculate Ki values. The experiments were repeated three separate times, each time in duplicate. Data are presented as mean values±sd.
Figure 3B:
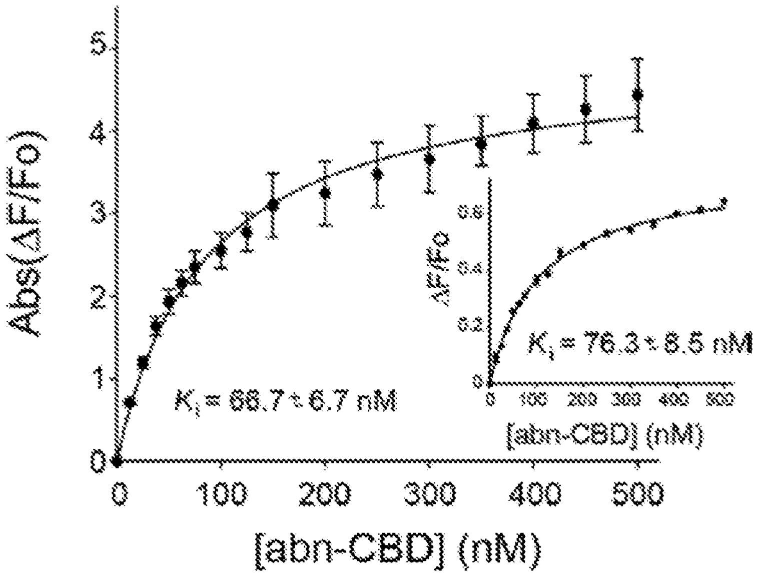

To determine the potency of abn-CBD interaction with CRBP1, we titrated CRBP1/atROL complex with increasing concentrations of the ligand (FIG. 3A). Changes in the fluorescence of the protein or the retinoid moiety plotted as a function of abn-CBD concentration were best fitted with a one-site saturation-binding model. The value of the inhibition constant (Ki) was calculated to be ~67 nM. (FIG. 3B). In the reverse experiment, CRBP1 loaded with abn-CBD was titrated with atROL. In this setting, the Ki value for replacing abn-CBD by vitamin A was –34 nM, indicating that the affinity of abn-CBD for CRBP1 is comparable to the endogenous ligand.

Figure 4A:
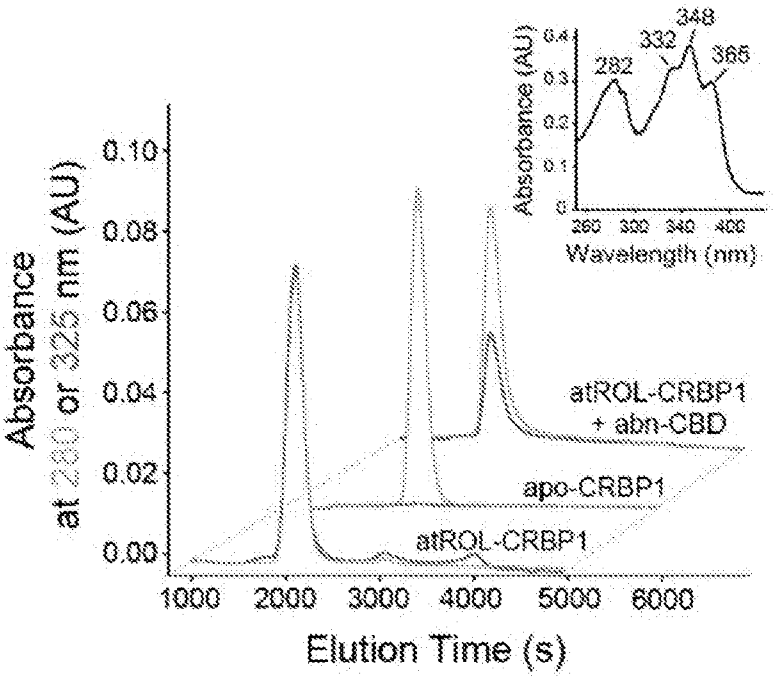
FIGS. 4(A-C) illustrate plots and graphs showing biochemical evaluation of the interaction of CRBP1 with abn-CBD. (A) Incubation of vitamin A-bound CRBP1 with abn-CBD led to depletion of atROL as evident by decreased absorption at 325 nm in relation to the protein absorbance at 280 nm in the repurified sample. (inset) UV/vis absorbance spectrum of atROL-bound CRBP1. (B) MS-based detection of abn-CBD in the CRBP1 fractions. The extracts of the protein samples preincubated abn-CBD and repurified revealed presence of intense ion peak at m/z=315.2 $[M+H]^+$. The molecular identification of this parent ion as corresponding to abn-CBD was achieved by comparing the MS/MS fragmentation pattern with a synthetic standard of the ligand. (C) Quantification of the ligand/protein ratios after incubation of vitamin A-bound CRBP1 with 2 molar excess of abn-CBD. The degree of atROL elimination from the protein is proportional to the amount of abn-CBD bound suggesting that these two ligands compete for the same binding site.
Figure 4B:
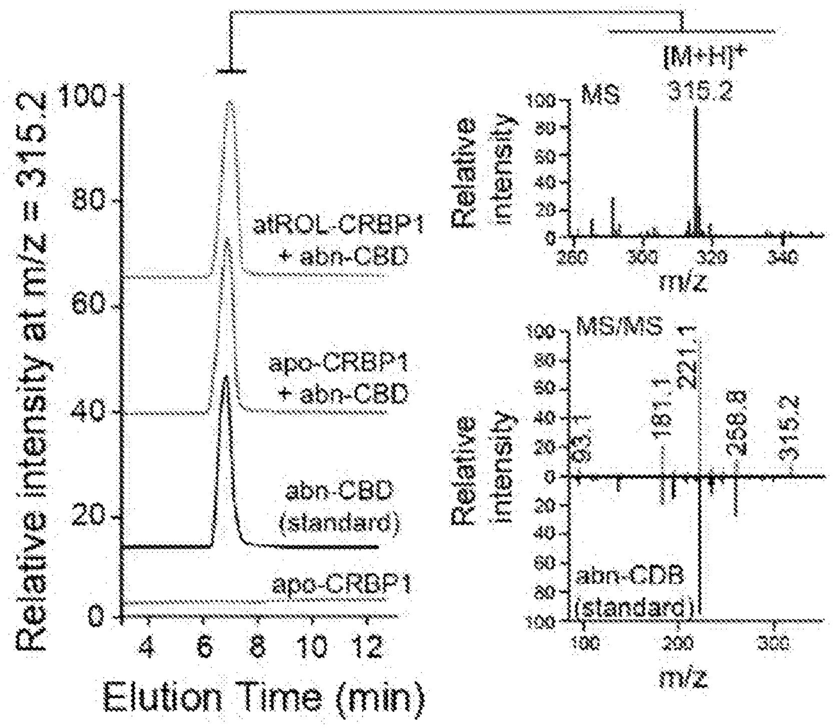
Figure 4C:
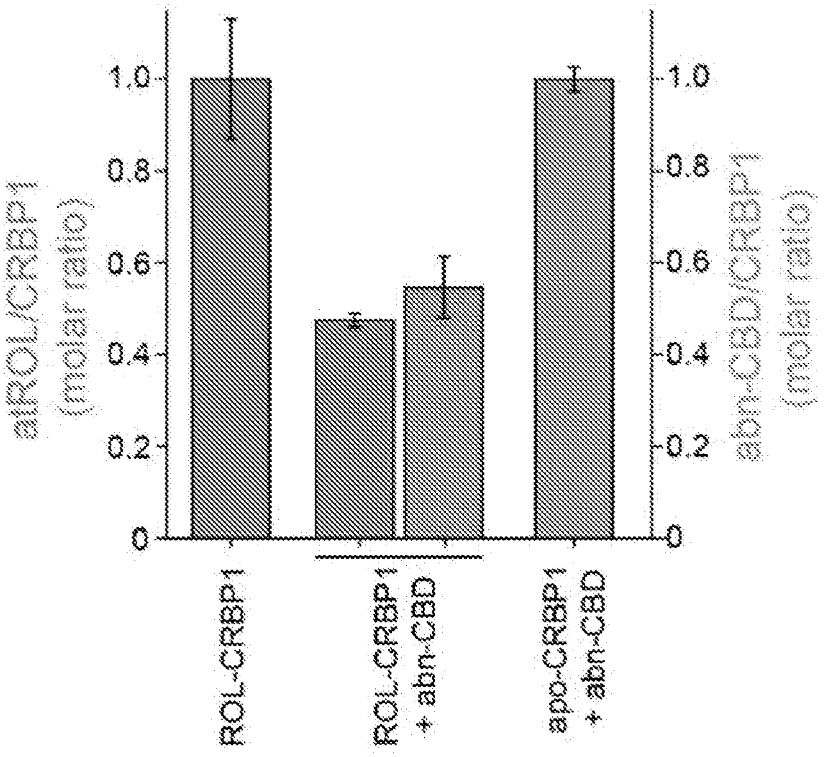

Although suggestive, changes in the fluorescence of CRBP1 upon titration with a nonretinoid ligand do not provide information on whether the retinoid liberation is caused by a direct competition of abn-CBD for the vitamin A binding site. To validate the fluorescence data and further investigate the interaction of abn-CBD with CRBP1, the protein prebound to atROL was incubated with the cannabinoid in a 1:2 molar ratio and repurified on an ion exchange column. The lipid composition carried by the protein at the end of the experiment was analyzed by liquid chromatography/mass spectrometry (LC/MS). Consistent with the fluorescence data, the incubation of holo-CRBP1 with abn-CBD resulted in diminished absorbance at 325 nm as compared to the control sample, indicating the loss of the retinoid (FIG. 4A). To attest whether the removal of atROL was accompanied by the binding of abn-CBD, we extracted lipids associated with the repurified protein with hexane and examined their composition. As shown in FIG. 4B, abn-CBD was readily detectable in the samples obtained from the incubation of apo- or holo-CRBP1 with this compound. Notably, the quantification of atROL and abn-CBD indicated the proportional replacement of the retinoid by the cannabinoid (FIG. 4C). These biochemical data suggest that abn-CBD interacts tightly with CRBP1, causing the replacement of vitamin A from the protein's binding site and, thus, acting as a competitive inhibitor of this carrier protein.

The Structure of CRBP1 in Complex with abn-CBD

Figure 5A:
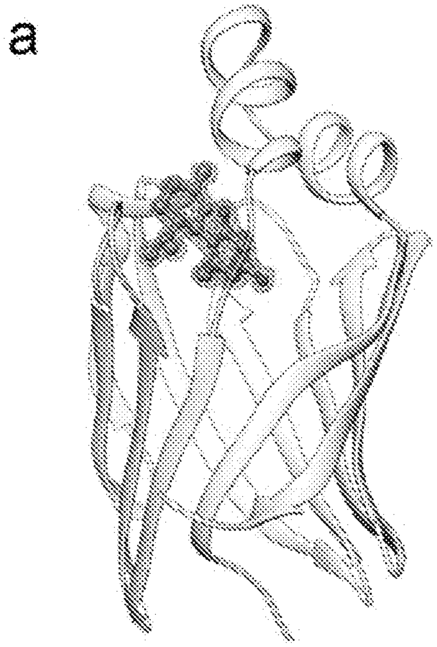
FIGS. 5(A-D) illustrate crystal structure of CRBP1 in complex with abn-CBD. (A) Ribbon representation of the overlay structures of CRBP1 (PDB No. 6E5L). Position of abn-CBD is indicated by ball-and-stick model of the ligand. The mesh corresponds to the 2Fo−Fc electron density map contoured at 1.2σ. (B) Molecular organization of the abn-CBD binding pocket with selected residues present in the vicinity or interacting with the ligand. Ordered water molecules (W) are shown as spheres; dashed lines indicate hydrogen bonds. Distances are shown in angstroms. (C) Superimposed structures of CRBP1 in complex with atROL (PDB No. 5HBS) or abn-CBD (PDB No. 6E5L). Spatial positions of amino acids within the binding site are nearly identical in both structures, suggesting that interaction with abn-CBD provokes similar conformational changes in CRBP1 as observed for atROL. (D) Comparison of the ligands' positions within the binding pocket of CRBP1. The hydroxylated aromatic ring of abn-CBD utilizes a part of the binding cavity that is not occupied by the retinoid moiety.

To obtain insight into the molecular aspect of the interaction between CRBP1 and its nonretinoid ligand, we crystallized this protein in the presence of abn-CBD and solved the complex structure at 1.17 Å resolution (PDB No. 6E5L). The electron density of the ligand was readily observed and well-defined, allowing for the unambiguous modeling of abn-CBD molecules inside the binding pocket of the protein (FIGS. 5A,B). As predicted by the biochemical data, abn-CBD binds in the same binding cavity as atROL. Remarkably, the interaction of CRBP1 with the cannabinoid dramatically decreased the flexibility of the protein's portal region (residues 24-36, 53-60, and 73-81) by inducing identical conformational changes as observed upon binding of vitamin A. Also, the averaged B-factor calculated for the main chain of the portal region dropped from 30.6 Å2 for apo-CRBP1 (PDB No. 5H9A) to 9.8 Å2 upon abn-CBD binding. This value is comparable to that observed for the protein in complex with atROL (10.5 A2, PDB No. 5H8T).

Figure 5B:
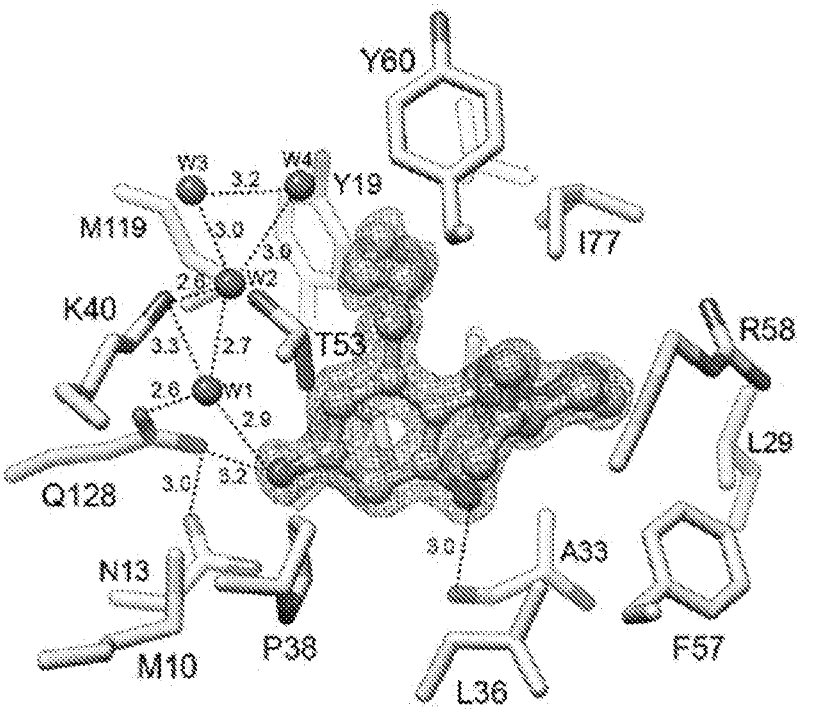
Figure 5C:
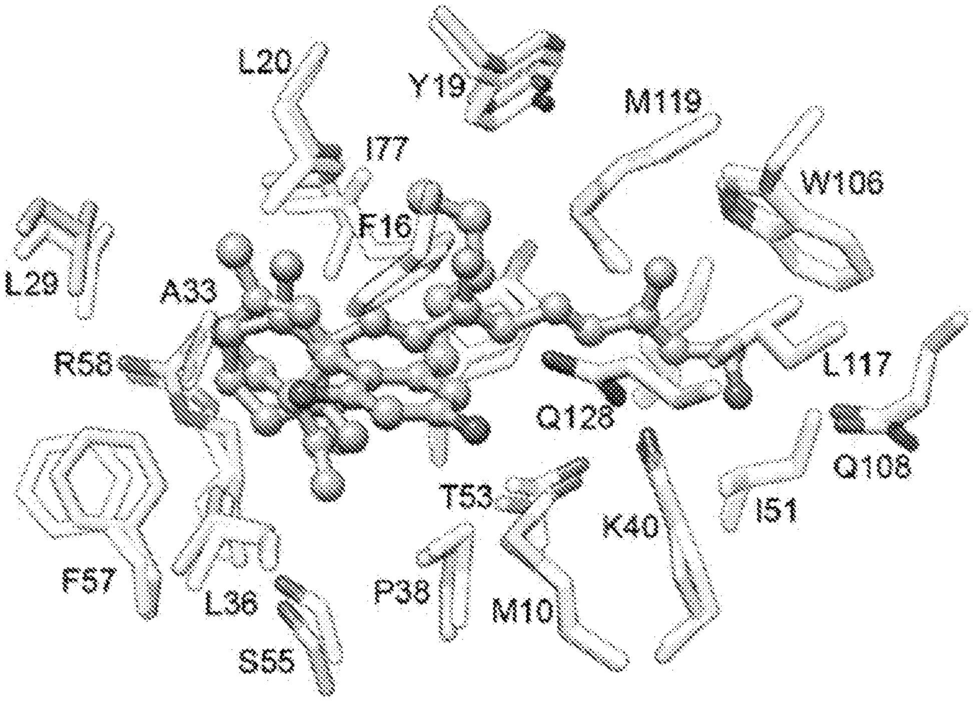
Figure 5D:
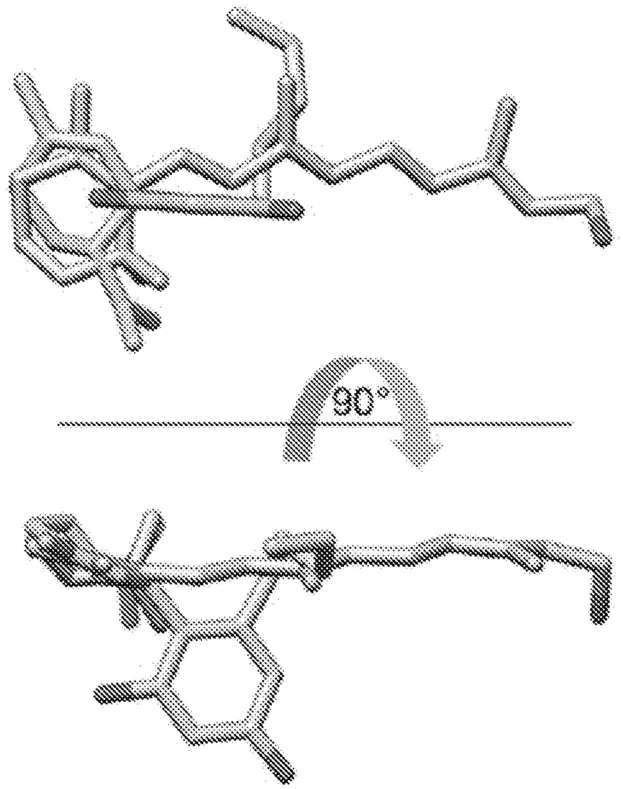

However, despite promoting identical conformational changes upon binding, the mode of interaction with the protein differs considerably for atROL and abn-CBD (FIG. 5C,D). Although the comparison of the spatial position of these two ligands revealed overlap between the orientation of the β-ionone and the cyclohexene rings, the substituted aromatic ring of abn-CBD is positioned in a part of the binding cavity that is normally not occupied by the retinoid moiety. Importantly, this part of abn-CBD makes specific contacts by forming hydrogen bonds with the main and side chains of residues within the binding pocket (FIG. 5B). The hydroxyl group in the ortho position (with respect to the cyclohexene ring) forms a single hydrogen bond with the carboxyl oxygen of the Ala33, whereas the para-hydroxyl is part of an extensive network of hydrogen bonds that involve the side chains of Asn13, Lys40, and Gln128 as well as at least four ordered water molecules. Lastly, the aliphatic chain of abn-CBD occupies a hydrophobic cavity enclosed by the side chain of Phe16, Tyr19, Leu20, Ile77, and Met119 that is common with the binding site of the polyene chain of vitamin A.

The Correlation between the Ligands' Structures and Their Binding Affinities

Figure 6A:
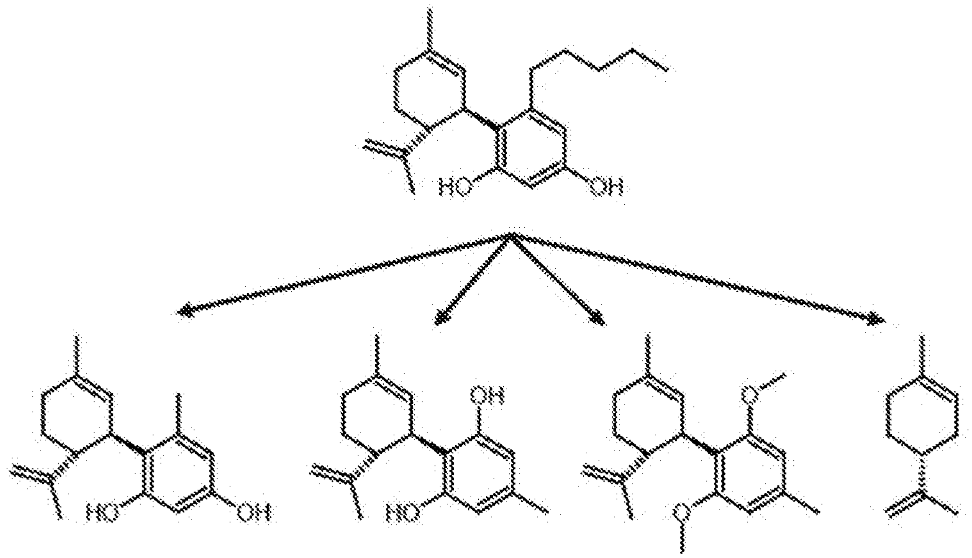
FIGS. 6(A-E) illustrate a relationship between structure of cannabinoid ligands and their affinity. (A) Chemical structures of abn-CBD derivatives used in the experiments. (B, C) Changes in the fluorescence emission spectra upon titration with abn-CBDO and CBDO, respectively. Ki values were calculated by fitting the experimental data to the one-site saturation ligand-binding model. (D) Interactions of abn-CBDO inside the binding cavity of CRBP1 as revealed by the X-ray crystallography (PDB No. 6E5T). (E) Orientation of CBDO inside of the binding pocket (PDB No. 6E6M). The absence of a hydroxyl group in the para position in CBDO determines weaker interaction of this ligand with CRBP1. The 2Fo-Fc electron density maps were contoured at 1.4σ. Ordered water molecules (W) are shown as red spheres; dashed lines indicate hydrogen bonds. Distances are shown in angstroms.
Figure 6B:
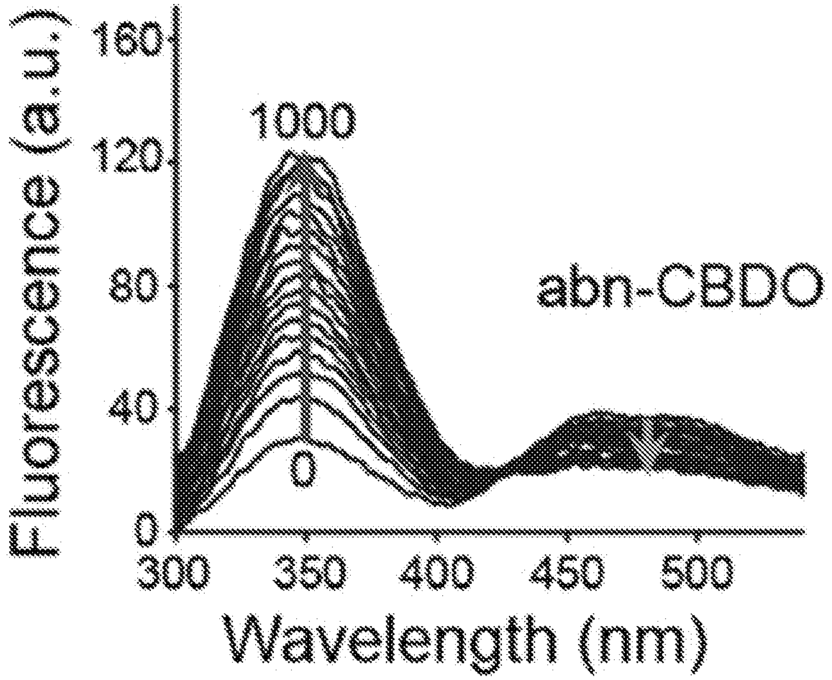
Figure 6B:
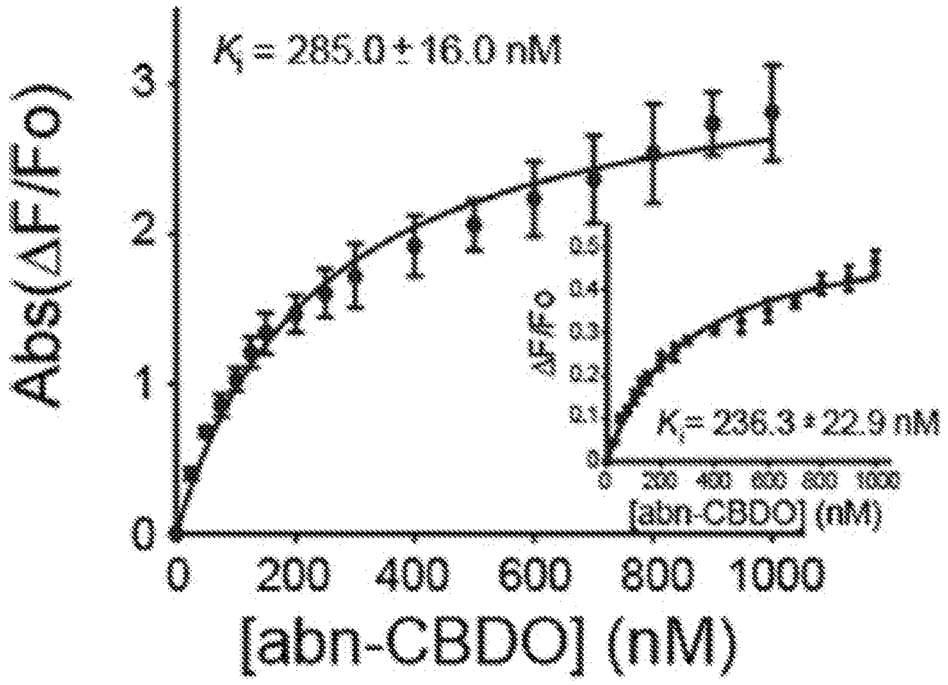
Figure 6C:
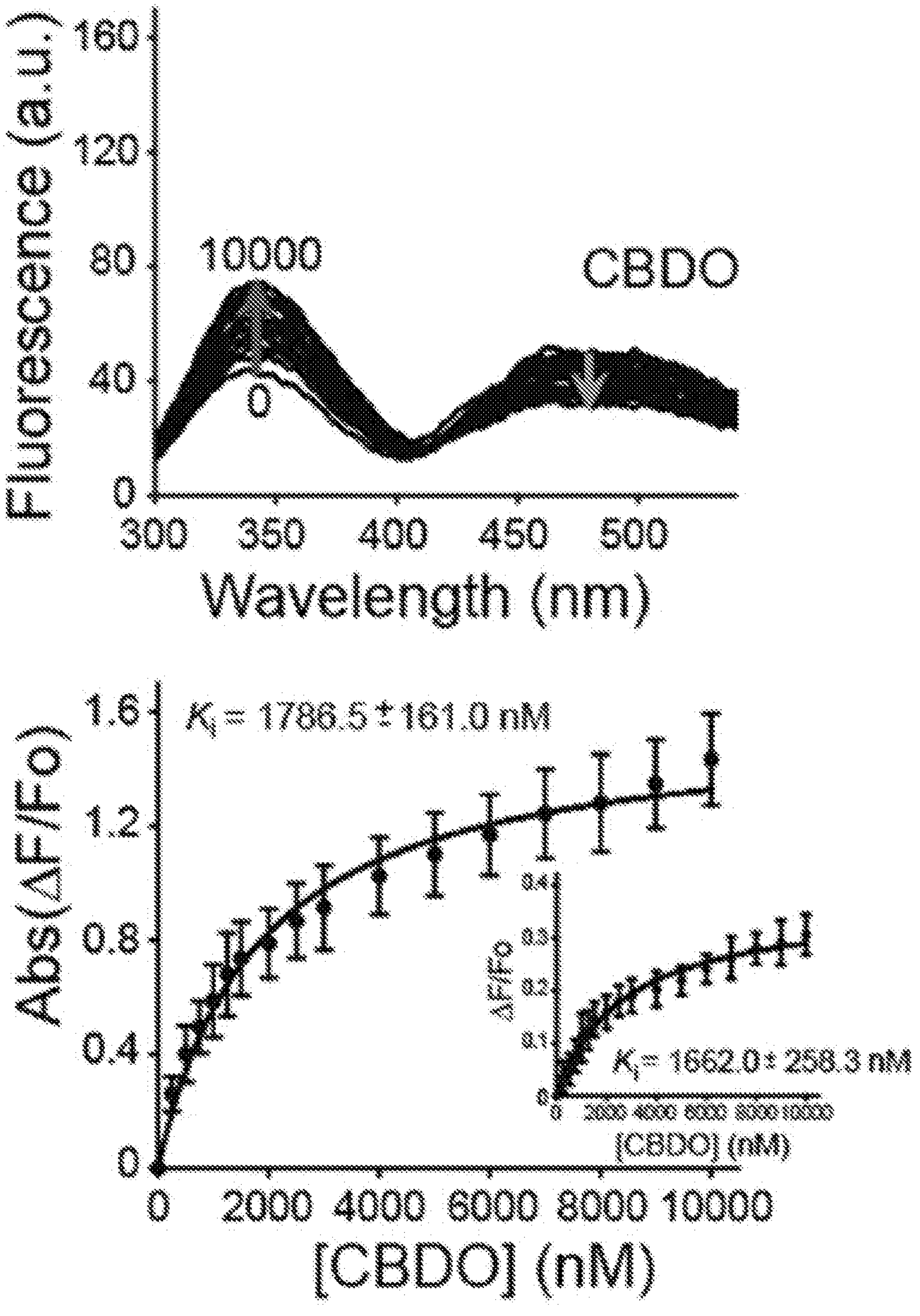
Figure 6C:
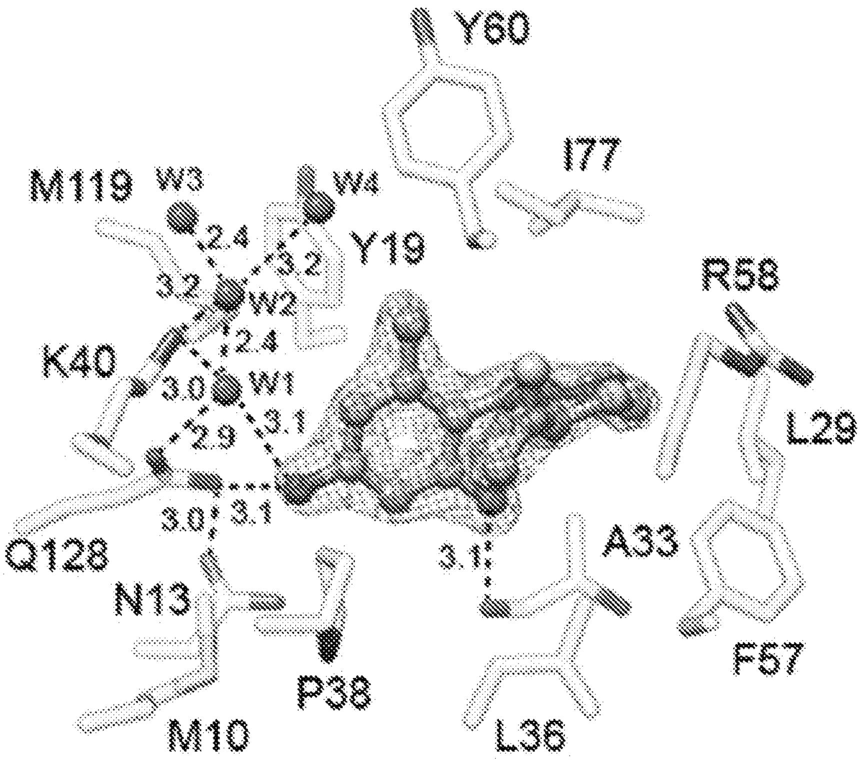

The structural data identified two types of interactions contributing to abn-CBD binding: hydrophobic that involve the cyclohexene ring and the pentyl aliphatic chain (analogous to the β-ionone ring and the polyene chain of vitamin A) and the hydrogen bond formation by the hydroxyl groups of the ligand. To dissect the relative contributions of these two modes of interaction to the Ki value of this ligand, we examined three derivatives of abn-CBD: abn-CBDO (5-methyl-4-[(1R,6R)-3-methyl-6-prop-1-en-2-ylcyclohex-2-en-1-yl]benzene-1,3-diol), in which the pentyl chain was shortened to a methyl group; CBDO (5-methyl-2-[(6R)-3-methyl-6-prop-1-en-2-ylcyclohex-2-en-1-yl]benzene-1,3-diol), in which positions of hydroxyl and methyl groups were swapped as compared to abn-CBDO; and O-1918 (1,3-dimethoxy-5-methyl-2-[(1R,6R)-3-methyl-6-prop-1-en-2-ylcyclohex-2-en-1-yl]benzene), which cannot form hydrogen bonds due to the methylation of its hydroxyl groups (FIG. 6A). The fluorescence atROL-replacing assay revealed major differences in the Ki values for these compounds. Compared with abn-CBD, shortening the aliphatic chain (represented by abn-CBDO) resulted in the apparent affinity being lowered by 4.3 times (FIG. 6B). Even more profound change was observed for CBDO. Switching positions of the para-hydroxyl and ortho-methyl groups caused a further 6.3-fold increase of the Ki value to ~1.7 μM (FIG. 6C). Finally, the inability of O-1918 to form hydrogen bonds abolished the meaningful binding of this derivative in the 0-10 μM range. Similarly, we did not observe limonene interacting (representing the cyclohexene portion of the ligand) with CRBP1. These data strongly suggest that, although abn-CBD competes for the same site with atROL, its high affinity is largely determined by the unique interactions inside the binding pocket that differ from those observed with vitamin A.

Figure 6D:
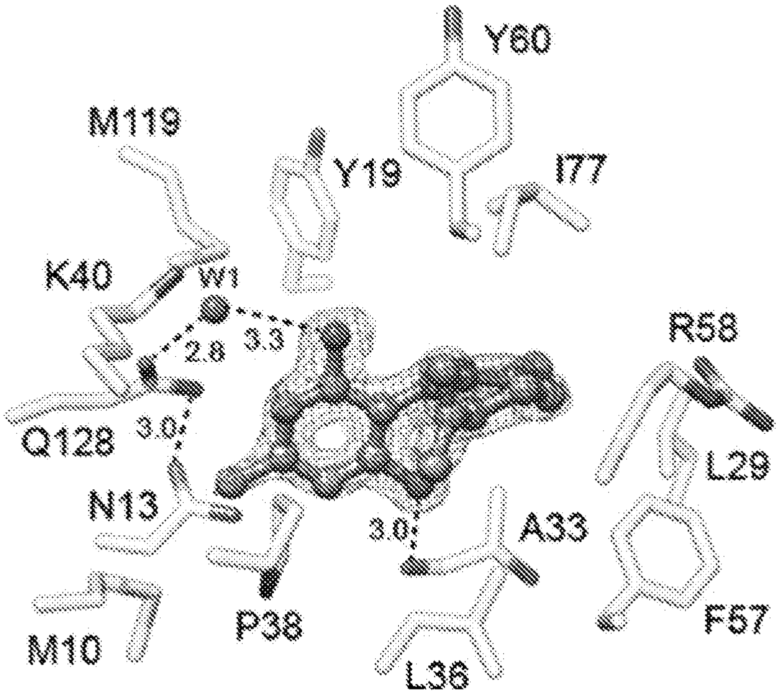

To better understand the correlation between the affinity of the abn-CBD derivatives and their binding modes, we cocrystallized CRBP1 with abn-CBDO or CBDO and determined structures of these complexes at 1.55 Å resolution, PDB No. 6E5T and PDB No. 6E6M, respectively). In both structures, the ligands were clearly identified based on their distinct residual electron densities (FIGS. 6D,E). The cyclohexene and aromatic moieties common to these compounds were found in essentially identical configurations inside the binding pocket. The only difference in binding modes between these two compounds was the extent to which they interact with the protein via hydrogen bonds. The absence of the para hydroxyl effectively eliminates the interaction of CBDO with the side chain of Gln128 and the ordered water molecules that were part of a larger network of hydrogen bonding seen in the abn-CBD and abn-CBDO complexes (FIG. 6B and FIG. 6D). This deficiency is neither compensated by the hydrogen bonds between the ortho hydroxyl and the main chain of Ala33 nor substituted by the involvement of the swapped hydroxyl group in a hydrogen bond with an isolated water molecule (FIG. 6E). Thus, the affinity and specificity of the interaction between abn-CBD and CRBP1 is not determined by the similarities to the retinoid moiety but the interactions of the hydroxyl substituents on the aromatic ring that are distinct from those observed for atROL.

The Interaction of abn-CBD with Other Members of the CRBP Protein Family

High structural similarity between CRBPs raises the question whether abn-CBD interacts specifically with CRBP1 or if it also binds to other members of this protein family. Although the structures of human CRBPs revealed highly similar binding cavities, there are several amino acid substitutions that might contribute to the selectivity of this ligand. Comparing the binding sites of CRBP1 and CRBP2 revealed four amino acid substitutions in the vicinity of abn-CBD: Leu20/Met, Pro38/Gln, Gly76/Ser, and Ile77/Leu. They do not affect the architecture of the binding cavity with the exception of Pro38/Gln. The much larger side chain of glutamine present in CRBP2 protrudes into the binding pocket and occupies part of the space, so that it cannot accommodate abn-CBD, and thus effectively disables binding of this compound. The absence of interaction between abn-CBD and CRBP2 was also evident in the fluorescence-binding assay. Consequently, we were not able to obtain crystals of CRBP2 in complex with this ligand.

The differences in the binding pocket of CRBP3 and CRBP4 as compared to CRBP1 are less profound (FIGS. 9A-D). They include substitutions of Phe16/Met and Ile77/Leu in CRBP3 and Leu20/Met, Phe57/Leu, and Ile77/Leu in CRBP4. As a result, these two proteins bind abn-CBD similarly to CRBP1. The crystal structures of CRBP3 and CRBP4 in complex with this ligand revealed that the orientation of abn-CBD within the binding pocket was nearly identical to that observed in CRBP1, PDB No. 6E5W and PDB No. 6E6K, respectively). A subtle shift in abn-CBD's position was seen in the complex with CRBP3, attributable to the smaller size of the Leu57 side chain, which eliminates some of the steric restraints that define the spatial position of the ligand's aromatic ring.

The Effect of abn-CBD on Ocular Vitamin A Metabolism

The physiological significance of CRBP1 stems from its role in the intracellular transport of vitamin A. CRBP1 is particularly important for the regeneration of visual chromophore. Highly expressed in the RPE cells, this carrier protein facilitates the reuptake of atROL from photoreceptor cells, enabling the efficient formation of all-trans-retinyl ester and its subsequent enzymatic conversion into 11-cis-retinol by RPE65. Consequently, studies on $Rbp1^{-/-}$ mice revealed a transient accumulation of atROL during the regeneration of visual chromophore after exposure to bright light. This well documented phenotype can serve as a reference for the investigation of the effect of CRBP1 inhibitors on retinoid metabolism in vivo.

Influencing retinoid metabolism in the eye requires the efficient delivery of an active compound to retina tissue. Thus, we first investigated whether abn-CBD crosses the retina/blood or RPE/blood barrier by directly measuring the quantity of this compound in the eye after intraperitoneal (i.p.) injection. Mouse eyes perfused with phosphate-buffered saline (PBS) were collected between 1 and 15 h after administration of a single dose of 15 mg $kg^{-1}$. Abn-CBD was readily detectable in the eye extracts by LC/MS. Using deuterated abn-CBD (d3-abn-CBD) as an internal standard, we determined that the ocular level of this compound reached the maximum value of 58 pmol/eye 2 h after the injection. Importantly, abn-CBD persisted in the ocular tissues for several hours post-treatment with a half-life of ~7 h. These results indicate that abn-CBD efficiently distributes into the eye targeting CRBPs expressed in the RPE and the retina.

Next, we examined the impact of abn-CBD on vitamin A metabolism in vivo. For this purpose, we analyzed the flow of retinoids via the visual cycle during the regeneration of visual chromophore after exposure to bright light. Dark-adapted mice were treated with 0.25 mg of the compound 1.5 h prior to exposure to a flash of light. The light intensity was set up to cause photoisomerization in 75% of rhodopsin as indicated by the decrease in the amount of 11-cis-retinal measured immediately after the light exposure (FIG. 7). As anticipated, the levels of all-trans-retinaldehyde increased transiently in the first minutes of the recovery and faded away, as the bolus of retinoid released by photoactivated rhodopsin was first reduced to atROL, which was subsequently transported to RPE cells, esterified by lecithin: retinol acyltransferase (LRAT), converted to 11-cis-retinol, and oxidized to the corresponding aldehyde.

Remarkably, the comparison of the time-resolved retinoid composition between the treated and the control groups of mice indicated no differences in the rate of all-trans-retinaldehyde clearance. However, transient accumulation of atROL became apparent in the presence of abn-CBD (FIGS. 7A,B). This prolonged persistence of atROL had a trickle-down effect on the accumulation of all-trans-retinyl esters in the RPE cells and their delayed enzymatic isomerization. Consequently, the rate of 11-cis-retinaldehyde regeneration was noticeably slower in the abn-CBD treated mice. Notably, the alteration in atROL clearance upon pharmacological treatment was comparable to what has been described for $Rbp1^{-/-}$ mice, suggesting that abn-CBD exerts its biological activity by targeting CRBP1 in vivo.

Abn-CBD does not Inhibit the Activities of Key Enzymes in the Visual Cycle

The transient accumulation of atROL upon the regeneration of visual chromophore might result from the off-target inhibition of LRAT, RPE65, or retinol dehydrogenases activities by abn-CBD. Thus, to further probe the biological effect of this compound, we tested its effect on the key enzymes of the visual cycle. For this purpose, microsomes isolated from bovine RPE cells were preincubated with 10-50 μM of abn-CBD (1:1 to 1:5 molar excess of cannabinoid) prior to the initiation of the esterification, isomerization, or oxidation reactions by addition of an adequate retinoid substrate. The initial rates of the reactions were calculated by quantifying products of the enzymatic assays by high-performance liquid chromatography (HPLC), abn-CBD did not cause a measurable decline in the enzymatic activities of LRAT, RPE65 or RDH5, further indicating that the delay in the regeneration of the visual chromophore in vivo results from blocking CRBP function, rather than interfering with the enzyme machinery of visual cycle.

The Impact of the CRBP1 Inhibitor on the Mouse ERG

Figure 7C:
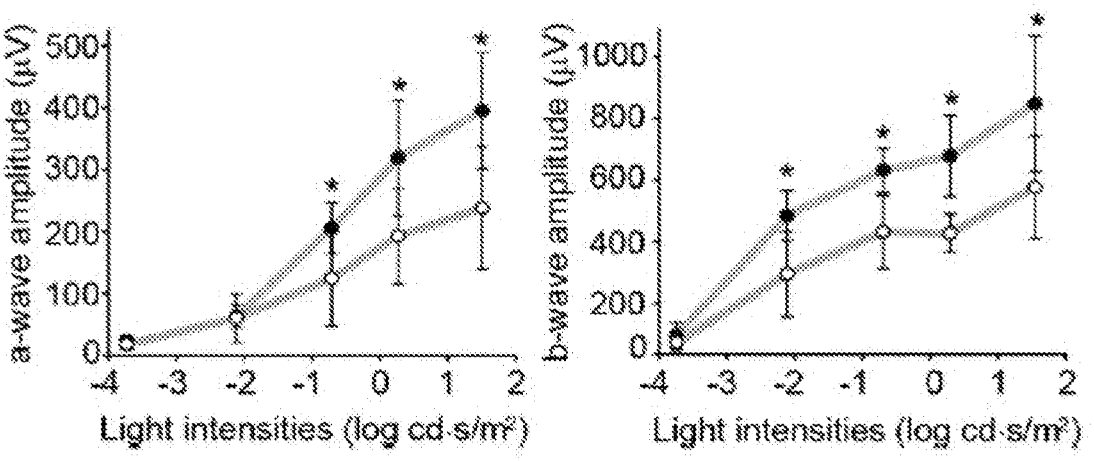

To quantify the effect of the CRBP1 inhibitor on the recovery of visual sensitivity after a light stimulus, we measured full-field electroretinography (ERG) responses in mice. Prior to the illumination, the animals were either treated with DMSO (vehicle) or abn-CBD. Both drugs were administrated in a dose of 30 mg $kg^{-1}$. Scotopic ERG responses at varying light intensities were recorded 4 h after the exposure to a flash of light that photobleached ~50% of the visual pigment. As illustrated in FIG. 7C, the recovery of both a-wave and b-wave amplitudes after light illumination in mice treated with abn-CBD is slower as compared to the untreated group of animals. However, even in a relatively high dose used in this experiment, the inhibitor of CRBP1 had much smaller impact on the visual cycle without causing its blockage, as it was reported for retinylamine and emixustat.

The Protective Effect of abn-CBD against Light-Induced Retinal Degeneration

Figure 8A:
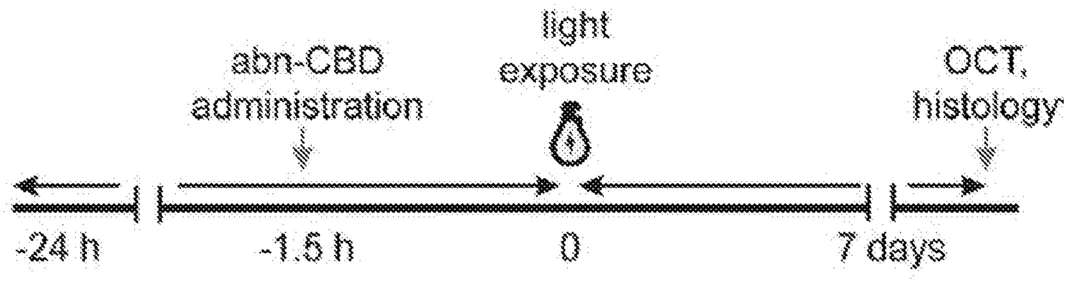
FIGS. 8(A-D) illustrate plots and images showing Abn-CBD protects against acute light-induced retinal degeneration in Balb/cJ mice. (A) Schematic representation of the experimental design. (B) Representative OCT images of the retinas for Balb/cJ mice not exposed to light (top) and animals pretreated with DMSO (vehicle) or abn-CBD (30 mg kg-1) and subjected to strong illumination (middle and bottom, respectively). The images indicate the protective effect of abn-CBD on photoreceptor cells. ONL, outer nuclear layer; INL, inner nuclear layer. Bars indicate 100 μm. (C) Quantification of the changes in the retinal morphology based on the thickness of the ONL of the OCT images (n=6). The retinal morphology was preserved by the CRBP1 inhibitor in a dose-dependent manner. (D) Representative retinal images of the inferior retina of Balb/cJ mice after light exposure. Severe retinal degeneration is observed 7 d post illumination in untreated mice, whereas systemic administration of abn-CBD resulted in partial preservation of the photoreceptor cells as compared to the eyes not exposed to light. OS, photoreceptor outer segments; IS, photoreceptor inner segments; OPL, outer plexiform layer; IPL, inner plexiform layer; GCL, ganglion cell layer. Bars indicate 50 μm.
Figure 8B:
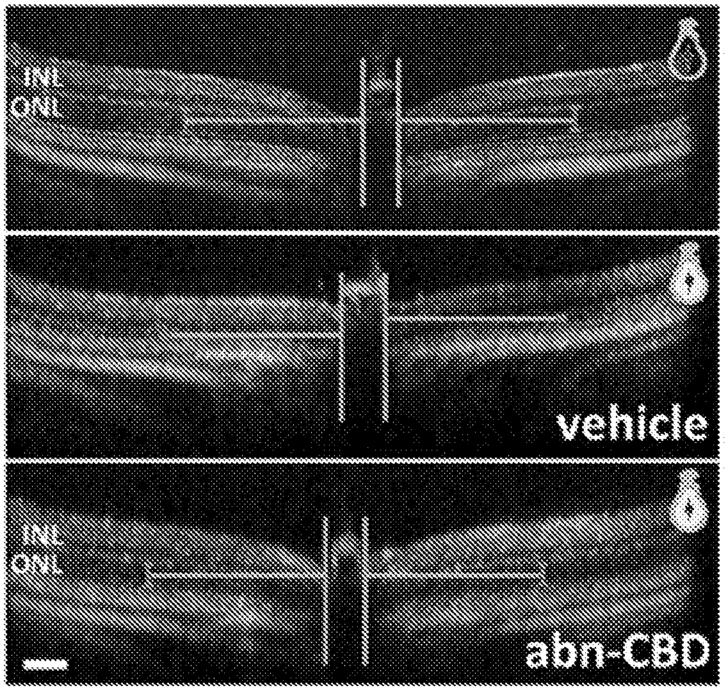
Figure 8C:
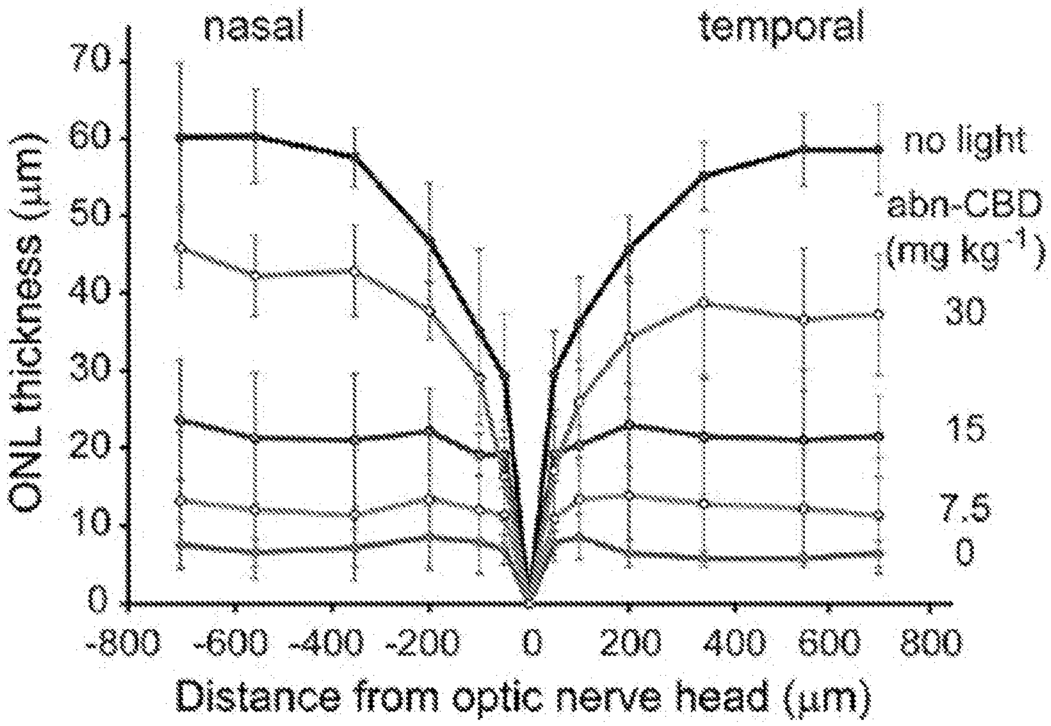
Figure 8D:
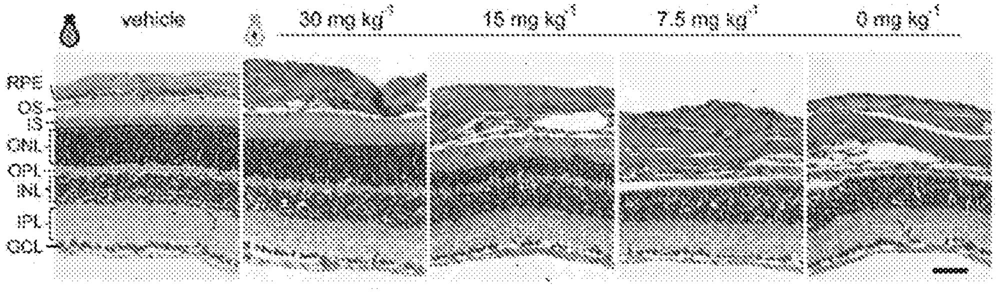
Figure 9A:
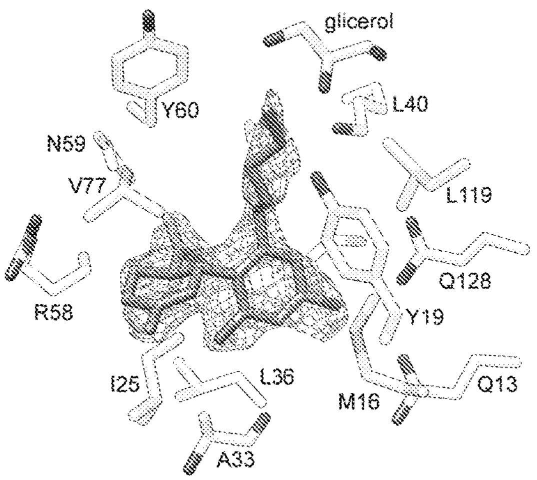
FIGS. 9(A-D) Structural basis for the abn-CBD's binding to CRBP3 and CRBP4. (A) Electron density maps for abn-CBD bound to CRBP3 (PDB No. 6E5W). (B) Electron density maps for abn-CBD bound to CBRP4, (PDB No. 6E6K). The meshes correspond to the $2F_o$-$F_c$ electron density maps, contoured at 1.2σ for both structures. (C) Close-up view of the ligand binding site of superimposed structures of CRBP1 and CRBP3 (PDB No 6E5L and 6E5W, respectively) in complex with abn-CBD. (D) Overlay of CRBP1 structures with CRBP4 (PDB No 6E6K) bound to abn-CBD.
Figure 9B:
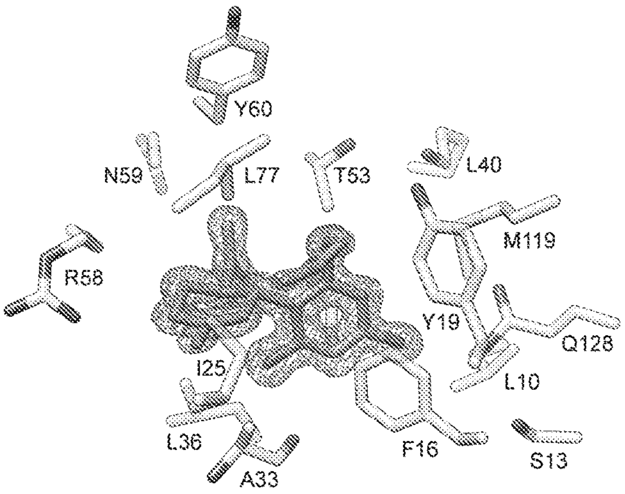
Figure 9C:
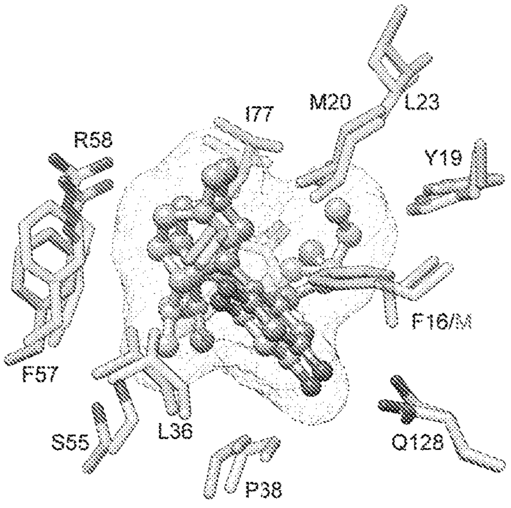
Figure 9D:
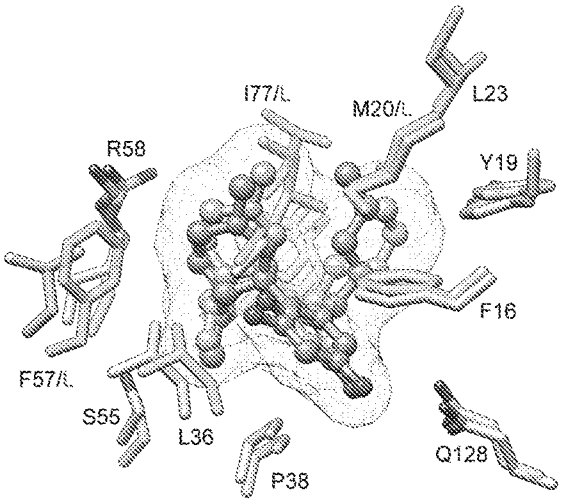

Retinaldehyde reactivity and the accumulation of its cytotoxic condensation products is an etiologic factor in retinal and macular degenerations of multiple causes. Thus, the regulation of the ocular metabolism of vitamin A was shown to be an effective strategy for control progress of a subset of ocular diseases resulting from a combination of certain environmental insults, such as prolonged exposure to intense light. The ability of CRBP1 inhibitors to modulate visual cycle retinoid flow represents an alternative strategy to protect the retina from the cytotoxicity of retinal and its metabolites. Thus, to examine the effectiveness of abn-CBD in protection against retinal phototoxicity, we administered this compound to Balb/cJ mice by IP injection 1.5 h prior to exposure to white light of sufficient intensity to cause retinal damage in the absence of the treatment. A week later, the integrity of the retinas was examined in vivo by optical coherence tomography (OCT) followed by a morphological analysis of the isolated mouse eyes. As shown in FIG. 8A, exposure to bright light caused severe retinal degeneration in the untreated mice as exemplified by the diminished thickness of the outer nuclear layer (ONL) and the deterioration of the cellular organization of the retinas. Notably, the animals pretreated with abn-CBD were largely protected against the light-induced retinal damage, as their retinal morphologies closely resembled those of mice not exposed to light. The protective effect of abn-CBD was dose-dependent with the estimated dose causing 50% of maximum effect (ED50) ~15 mg $kg^{-1}$ (FIGS. 8B,C). To confirm the results obtained from the in vivo analyses, we performed a histological examination of retinal sections after Hemotoxylin and Eosin (H&E) staining. The diminished ONL thickness in DMSO-treated mice exposed to bright light as well as the protective effect of treatment with abn-CBD agreed with the findings from the OCT imaging (FIG. 8D). Altogether, these data indicate that the modulation of ocular retinoid metabolism by the CRBP1 antagonist or inhibitor is effective in alleviating pathophysiological changes resulting from the overstimulation of the photoreceptors and retinaldehyde toxicity.

In summary, we have identified compounds that targets selected CRBPs and, thus, influences retinoid metabolism in vivo. Abn-CBD, an antagonist of these vitamin A chaperones, showed efficacy in protecting mouse retinas from light-induced retinal degeneration.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A method of treating light induced retinal degeneration in a subject in need thereof, comprising administering to the subject, an antagonist of cellular retinol binding protein 1 (CRBP1), wherein the CRBP1 antagonist is abnormal cannabidiol (abn-CBD) compound of formula (IV):

(IV)

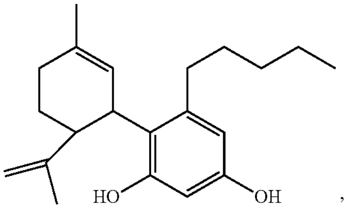

, or abn-CBD compound of formula (V):

(V)

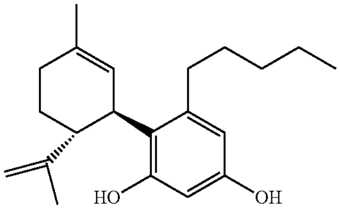

2. The method of claim 1, wherein the CRBP1 antagonist is abn-CBD compound of formula (IV)

(IV)

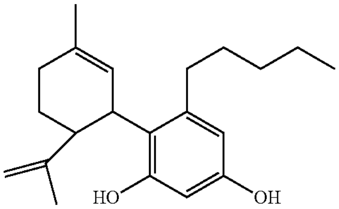

3. The method of claim 1, wherein the CRBP1 antagonist is abn-CBD compound of formula (V)

(V)

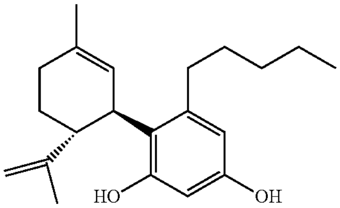

4. The method of claim 1, wherein the CRBP1 antagonist is administered systemically.

* * * * *